United States Patent
King et al.

(10) Patent No.: US 12,162,992 B2
(45) Date of Patent: Dec. 10, 2024

(54) MICROORGANISMS FOR WASTE TREATMENT

(71) Applicant: MICROBIAL DISCOVERY GROUP, LLC, Franklin, WI (US)

(72) Inventors: Michael R. King, Oak Creek, WI (US); Sona Son, Franklin, WI (US); Claire Heile, Franklin, WI (US)

(73) Assignee: MICROBIAL DISCOVERY GROUP, LLC, Franklin, WI (US)

( * ) Notice: Subject to any disclaimer, the term of this patent is extended or adjusted under 35 U.S.C. 154(b) by 0 days.

(21) Appl. No.: 18/300,040

(22) Filed: Apr. 13, 2023

(65) Prior Publication Data

US 2024/0002626 A1    Jan. 4, 2024

Related U.S. Application Data

(63) Continuation of application No. 16/760,949, filed as application No. PCT/US2018/058948 on Nov. 2, 2018, now Pat. No. 11,634,554.

(60) Provisional application No. 62/687,610, filed on Jun. 20, 2018, provisional application No. 62/580,926, filed on Nov. 2, 2017.

(51) Int. Cl.
| | |
|---|---|
| *C12N 1/20* | (2006.01) |
| *C08J 11/10* | (2006.01) |
| *C12N 1/16* | (2006.01) |

(52) U.S. Cl.
CPC ............ *C08J 11/105* (2013.01); *C12N 1/20* (2013.01); *C08J 2323/06* (2013.01)

(58) Field of Classification Search
CPC ............ C12N 1/26; C12N 1/20; C12N 1/205
See application file for complete search history.

(56) References Cited

U.S. PATENT DOCUMENTS

| | | |
|---|---|---|
| 9,175,258 B2 | 11/2015 | Bywater-Ekegard |
| 9,410,213 B2 | 8/2016 | Matheny |
| 11,634,554 B2 * | 4/2023 | King ................ C12N 1/26 521/47 |
| 2017/0166466 A1 | 6/2017 | King et al. |

FOREIGN PATENT DOCUMENTS

| | | |
|---|---|---|
| CN | 101159102 A | 4/2008 |
| CN | 103980535 A | 8/2014 |
| CN | 109497281 A | 3/2019 |
| WO | 20120101528 | 8/2012 |
| WO | 2014067081 A | 5/2014 |
| WO | 20140172520 | 10/2014 |
| WO | 2019/090068 A1 | 5/2019 |
| WO | 2020/072578 A1 | 4/2020 |
| WO | 2023/018686 A1 | 2/2023 |

OTHER PUBLICATIONS

International Search Report and Written Opinion for PCT/US2018/058948, dated Jan. 18, 2019, 8 pages.
Miller et al. "Sanitary Landfill Simulation: Test Parameters and Simulator Conceptual Design," Naval Facilities Engineering Command: Civil Engineering Laboratory, Oct. 20, 1976 (Oct. 20, 1976), pp. 1-47.
Fei et al. "A laboratory landfill simulator for physical, geotechnical, chemical and microbial characterization of solid waste biodegradation processes," Coupled Phenomena in Environmental Geotechnics, May 30, 2013 (May 30, 2013), Taylor & Francis Group, London, pp. 321-327.
Mahar et al. "Modeling and simulation of landfill gas production from pretreated MSW landfill simulator," Frontiers of Environmental Science & Engineering, Apr. 15, 2014 (Apr. 15, 2014), vol. 10, Iss. 1, pp. 159-167.
"Bacillus Strains Improving Health and Performance of Production Animals", ED—Darl Kuhn, ip.com, ip.com Inc., West Henrietta, NY, US, (Feb. 11, 2016), XP013170586, ISSN: 1533-0001.
Partial supplementary European search report for counterpart EP Application No. 20858946.5, dated Aug. 23, 2023.
Sonune Nilesh et al.: "Isolation, characterization and identification of extracuricular enzyme producer Bacillus licheniformis from municipal wastewater and evaluation of their biodegradability", Biotechnology Research and Innovation, vol. 2, No. 1, (Jan. 1, 2018), pp. 37-44, XP055803907.

* cited by examiner

Primary Examiner — Tekchand Saidha
(74) Attorney, Agent, or Firm — Barnes & Thornburg LLP

(57) ABSTRACT

The invention relates to treatment of waste with one or more microorganisms for the purposes of, including but not limited to, degrading waste, bioremediation of waste, enhancing waste stabilization, reducing contaminants in waste, reducing odor in waste, reducing organics in waste, and combinations thereof. More particularly, the invention relates to isolated *Bacillus* strains, and strains having all of the identifying characteristics of these strains, and combinations thereof, for uses comprising the above-mentioned uses.

21 Claims, 9 Drawing Sheets

MICROORGANISMS FOR WASTE TREATMENT

CROSS-REFERENCE TO RELATED APPLICATIONS

This application is a continuation of U.S. application Ser. No. 16/760,949, filed on May 1, 2020 which is a national stage entry made under 35 U.S.C. § 371 of PCT International Application No. PCT/US2018/058948, filed Nov. 2, 2018, which claims under 35 U.S.C. § 119(e) the benefit of and priority to U.S. Patent Application No. 62/687,610, filed Jun. 20, 2018, and U.S. Patent Application No. 62/580,926, filed Nov. 2, 2017, the entire disclosures of which are incorporated by reference herein.

FIELD OF THE DISCLOSURE

The invention relates to treatment of waste with one or more microorganisms for the purposes of, including but not limited to, degrading waste, bioremediation of waste, enhancing waste stabilization, reducing contaminants in waste, reducing odor in waste, reducing organics in waste, and combinations thereof. More particularly, the invention relates to isolated *Bacillus* strains, and strains having all of the identifying characteristics of these strains, and combinations thereof, for uses comprising the above-mentioned uses.

BACKGROUND AND SUMMARY OF THE INVENTION

The present invention relates to microorganisms for use in waste treatment including, but not limited to, the bioremediation of industrial waste, municipal solid waste, landfill waste, soil waste, wastewater, composting waste, contaminated groundwater, leachate from waste, polymer-containing waste, hydrocarbon-containing waste, a plastic-containing waste, a polyethylene-containing waste, a high density polyethylene-containing waste and plastic bag-containing waste, and methods of their use (e.g., the bioaugmentation of contaminated waste, soil, and water). The ability of microbial strains, such as *Bacillus* strains, to produce beneficial enzymes, and their antimicrobial activity and environmental compatibility, have led to the use of these microbial strains in waste treatment. For example, beneficial microbial strains can be used to reestablish the balance of bacteria beneficial to the environment and degrade harmful organic compounds in waste.

As plastics have been in production for less than 200 years, little information has been obtained concerning the rate of decomposition. Polymer crystallinity can limit chain movement and decreases the availability to degradative agents (including microbial enzymes) and increases hydrophobicity. Plastic oxidation and degradation can be initiated by ultraviolet photodegradation, thermooxidation, or by microbial or fungal-biosurfactant/enzyme production and biofilm formation. Following oxidation and the breakdown of weakened polymer chains, microorganisms and fungi are able to metabolize the plastic and convert the carbon to carbon dioxide.

Applicant has developed *Bacillus* strains, and combinations thereof, that are useful for waste treatment, waste degradation (including plastic-containing waste) and controlling the detrimental effects of waste, such as by removing a pollutant. These strains can increase the rate of decay of plastic waste (e.g., high-density polyethylene), degrade municipal solid waste, enhance waste stabilization, reduce contaminants in waste, reduce chemical oxygen demand, reduce organics in waste (e.g., hydrocarbons), reduce odor in waste (e.g., hydrogen sulfide and sulfate), and the like. In one embodiment a method of treating waste to remove a pollutant is provided. The method comprises contacting the waste with an effective amount of an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof, and removing the pollutant.

In another embodiment, a method of controlling a detrimental effect of waste is provided. The method comprises contacting the waste with an effective amount of an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof, and controlling the detrimental effect of the waste.

In various other embodiments, a commercial package, an additive for waste, and a composition are provided. The commercial package, additive for waste, and composition comprise an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the EXAMPLES are applicable to any of the following embodiments of the invention described in the numbered clauses below.

1. A method of treating waste to remove a pollutant, the method comprising contacting the waste with an effective amount of an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954

(NRRL No. B-67474), *Bacillus* strain 2310 (NRRL No. B-67471), a strain having all of the identifying characteristics of *Bacillus* strain 2310 (NRRL No. B-67471), and combinations thereof, and removing the pollutant.

2. The method of clause 1 wherein the waste is selected from the group consisting of industrial waste, municipal solid waste, landfill waste, soil waste, wastewater, composting waste, contaminated groundwater, leachate from waste, polymer-containing waste, hydrocarbon-containing waste, a plastic-containing waste, a polyethylene-containing waste, a high density polyethylene-containing waste, and plastic bag-containing waste.

3. The method of clause 1 or 2 wherein the pollutant is plastic.

4. The method of any one of clauses 1 to 3 wherein the pollutant is a polyethylene.

5. The method of clause 4 wherein the pollutant is a high-density polyethylene.

6. The method of any one of clauses 1 to 5 wherein the pollutant is an organic compound.

7. The method of clause 6 wherein the organic compound is removed by degradation.

8. The method of any one of clauses 1 to 2 wherein the pollutant is an inorganic compound.

9. The method of any one of clauses 1 to 8 wherein at least one of the *Bacillus* strains has antimicrobial activity.

10. The method of clause 9 wherein the antimicrobial activity is against bacteria selected from the group consisting of *E. coli, Salmonella, Staphylococcus, Enterococcus, Clostridia, Campylobacter*, and combinations thereof.

11. The method of any one of clauses 1 to 10 wherein the *Bacillus* strain produces an enzyme selected from the group consisting of an a hydrolase, an oxioreductase, a galactosidase, an NSPase, a phytase, an arabinoxylanase, a cellulase, a hemicelluase, a protease, an amylase, a xylanase, an esterase, a lipase, and combinations thereof.

12. The method of clause 11 wherein the enzyme is an esterase.

13. The method of clause 11 wherein the enzyme is a lipase.

14. The method of any one of clauses 1 to 13 further comprising treating the waste with another bacterial strain selected from the group consisting of another *Bacillus* strain, a lactic acid bacterial strain, and combinations thereof.

15. The method of any one of clauses 1 to 14 wherein the strain is *Bacillus* strain 8992 (NRRL No. B-67472), or a strain having all of the identifying characteristics of *Bacillus* strain 8992 (NRRL No. B-67472).

16. The method of any one of clauses 1 to 14 wherein the strain is *Bacillus* strain 2112 (NRRL No. B-67473), or a strain having all of the identifying characteristics of *Bacillus* strain 2112 (NRRL No. B-67473).

17. The method of any one of clauses 1 to 14 wherein the strain is *Bacillus* strain 2310 (NRRL No. B-67471), or a strain having all of the identifying characteristics of *Bacillus* strain 2310 (NRRL No. B-67471).

18. The method of any one of clauses 1 to 14 wherein the strain is *Bacillus* strain 4954 (NRRL No. B-67474), or a strain having all of the identifying characteristics of *Bacillus* strain 4954 (NRRL No. B-67474).

19. The method of any one of clauses 1 to 14 wherein the strain is *Bacillus* strain 8992 (NRRL No. B-67472).

20. The method of any one of clauses 1 to 14 wherein the strain is *Bacillus* strain 2112 (NRRL No. B-67473).

21. The method of any one of clauses 1 to 14 wherein the strain is *Bacillus* strain 2310 (NRRL No. B-67471).

22. The method of any one of clauses 1 to 21 wherein the effective amount of the *Bacillus* strain is about $1.0 \times 10^2$ CFU/gram of the waste to about $1.0 \times 10^6$ CFU/gram of the waste.

23. The method of any one of clauses 1 to 21 wherein the effective amount of the *Bacillus* strain is about $1.0 \times 10^2$ CFU/gram of the waste to about $1.0 \times 10^4$ CFU/gram of the waste.

24. The method of any one of clauses 1 to 21 wherein the effective amount is an amount greater than about $1.0 \times 10^2$ CFU/gram of the waste to about $1.0 \times 10^3$ CFU/gram of the waste.

25. The method of any one of clauses 1 to 24 further comprising contacting the waste with an enzyme selected from the group consisting of a hydrolase, an oxioreductase, a galactosidase, an arabinoxylanase, a protease, a lipase, an esterase, an amylase, a hemicellulase, an arabinoxylanase, a xylanase, a cellulase, an NSPase, a phytase, and combinations thereof.

26. A method of controlling a detrimental effect of waste, the method comprising contacting the waste with an effective amount of an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof, and controlling the detrimental effect of the waste.

27. The method of clause 26 wherein the waste is selected from the group consisting of industrial waste, municipal solid waste, landfill waste, soil waste, wastewater, composting waste, contaminated groundwater, leachate from waste, polymer-containing waste, hydrocarbon-containing waste, a plastic-containing waste, a polyethylene-containing waste, a high density polyethylene-containing waste, and plastic bag-containing waste.

28. The method of clause 26 or 27 wherein the detrimental effect is caused by a plastic.

29. The method of any one of clauses 26 to 28 wherein the detrimental effect is caused by a polyethylene.

30. The method of clause 29 wherein the detrimental effect is caused by a high density polyethylene.

31. The method of any one of clauses 26 to 30 wherein the detrimental effect is caused by an organic compound.

32. The method of clause 31 wherein the organic compound is removed by degradation.

33. The method of any one of clauses 26 to 27 wherein the detrimental effect is caused by an inorganic compound.

34. The method of any one of clauses 26 to 33 wherein at least one of the *Bacillus* strains has antimicrobial activity.

35. The method of clause 34 wherein the antimicrobial activity is against bacteria selected from the group consisting of *E. coli, Salmonella, Staphylococcus, Enterococcus, Clostridia, Campylobacter*, and combinations thereof.

36. The method of any one of clauses 26 to 35 wherein the *Bacillus* strain produces an enzyme selected from the group consisting of a hydrolase, an oxioreductase, a galactosidase, an NSPase, a phytase, an arabinoxylanase, a cellulase, a hemicellulase, a protease, an amylase, a xylanase, an esterase, a lipase, and combinations thereof.

37. The method of clause 36 wherein the enzyme is an esterase.

38. The method of clause 36 wherein the enzyme is a lipase.

39. The method of any one of clauses 26 to 38 further comprising treating the waste with another bacterial strain selected from the group consisting of another *Bacillus* strain, a lactic acid bacterial strain, and combinations thereof.

40. The method of any one of clauses 26 to 39 wherein the strain is *Bacillus* strain 8992 (NRRL No. B-67472), or a strain having all of the identifying characteristics of *Bacillus* strain 8992 (NRRL No. B-67472).

41. The method of any one of clauses 26 to 39 wherein the strain is *Bacillus* strain 2112 (NRRL No. B-67473), or a strain having all of the identifying characteristics of *Bacillus* strain 2112 (NRRL No. B-67473).

42. The method of any one of clauses 26 to 39 wherein the strain is *Bacillus* strain 2310 (NRRL No. B-67471), or a strain having all of the identifying characteristics of *Bacillus* strain 2310 (NRRL No. B-67471).

43. The method of any one of clauses 26 to 39 wherein the strain is *Bacillus* strain 4954 (NRRL No. B-67474), or a strain having all of the identifying characteristics of *Bacillus* strain 4954 (NRRL No. B-67474).

44. The method of any one of clauses 26 to 39 wherein the strain is *Bacillus* strain 8992 (NRRL No. B-67472).

45. The method of any one of clauses 26 to 39 wherein the strain is *Bacillus* strain 2112 (NRRL No. B-67473).

46. The method of any one of clauses 26 to 39 wherein the strain is *Bacillus* strain 2310 (NRRL No. B-67471).

47. The method of any one of clauses 26 to 39 wherein the strain is *Bacillus* strain 4954 (NRRL No. B-67474).

48. The method of any one of clauses 26 to 47 wherein the effective amount of the *Bacillus* strain is about $1.0 \times 10^2$ CFU/gram of the waste to about $1.0 \times 10^6$ CFU/gram of the waste.

49. The method of any one of clauses 26 to 47 wherein the effective amount of the *Bacillus* strain is about $1.0 \times 10^2$ CFU/gram of the waste to about $1.0 \times 10^3$ CFU/gram of the waste.

50. The method of any one of clauses 26 to 49 further comprising contacting the waste with an enzyme selected from the group consisting of a hydrolase, an oxioreductase, a galactosidase, an NSPase, a phytase, an arabinoxylanase, a cellulase, a hemicellulase, a protease, an amylase, a xylanase, an esterase, a lipase, and combinations thereof.

51. A commercial package comprising an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof.

52. An additive for waste comprising an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof.

53. A composition comprising an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of 2310 (NRRL No. B-67471), a strain having all of the identifying characteristics of *Bacillus* strain 2310 (NRRL No. B-67471), and combinations thereof.

54. The commercial package, additive, or composition of any one of clauses 51 to 53 wherein the *Bacillus* strain causes degradation of an organic compound or removal of an inorganic compound in waste.

55. The commercial package, additive, or composition of any one of clauses 51 54 wherein the *Bacillus* strain is in the form of a concentrate.

56. The commercial package, additive, or composition of any one of clauses 51 to 54 wherein the *Bacillus* strain is in the form of a superconcentrate.

57. The commercial package, additive, or composition of any one of clauses 51 to 56 wherein the *Bacillus* strain is in dry form.

58. The commercial package, additive, or composition of any one of clauses 51 to 57 wherein the *Bacillus* strain is in pelleted form.

59. The commercial package, additive, or composition of any one of clauses 51 to 56 wherein the strain is in a form selected from the group consisting of a powder, a liquid, and a pellet form.

60. The commercial package, additive, or composition of any one of clauses 51 to 59 further comprising a carrier for the *Bacillus* strain.

61. The commercial package, additive, or composition of clause 60 wherein the carrier is selected from the group consisting of salt, a dextrin, and combinations thereof.

62. The commercial package, additive, or composition of any one of clauses 51 to 61 in a bag.

63. The commercial package, additive, or composition of clause 62 wherein the bag is a plastic bag.

64. The commercial package, additive, or composition of any one of clauses 51 to 63 further comprising instructions for use of one or more of the *Bacillus* strains.

65. The commercial package, additive, or composition of any one of clauses 51 to 64 in a 20-pound bag.

66. The commercial package, additive, or composition of any one of clauses 51 to 64 in a 50-pound bag.

67. The commercial package, additive, or composition of any one of clauses 51 to 57 or 60 to 66 wherein the *Bacillus* strain is in powder form.

68. The commercial package, additive, or composition of any one of clauses 51 to 56 wherein the *Bacillus* strain is in liquid form.

69. The commercial package, additive, or composition of any one of clauses 51 to 68 wherein the *Bacillus* strain is in a container for commercial use.

70. The commercial package, additive, or composition of clause 69 wherein the container comprises plastic.

71. The commercial package, additive, or composition of clause 69 wherein the container comprises paper.

72. The commercial package, additive, or composition of any one of clauses 51 to 71 further comprising a binder.

73. The commercial package, additive, or composition of clause 72 wherein the binder is selected from the group consisting of clay, yeast cell wall components, aluminum silicate, and glucan, or combinations thereof.

74. The commercial package, additive, or composition of any one of clauses 51 to 73 wherein the *Bacillus* strain degrades a plastic.

75. The commercial package, additive, or composition of any one of clauses 51 to 74 wherein the *Bacillus* strain degrades a high density polyethylene.

76. The method of any one of clauses 26 to 50 wherein the detrimental effect is odor and the odor is controlled.

77. The method of clause 76 wherein the odor is caused by sulfate and hydrogen sulfide ($H_2S$) production.

78. A landfill simulator comprising at least four layers comprising a soil layer, a waste and soil layer, a drainage layer, and a filter.

79. The landfill simulator of clause 78 wherein the soil layer is compacted soil.

80. The landfill simulator of clause 78 or clause 79 wherein the drainage layer is granular.

81. The landfill simulator of any one of clauses 78 to 80 wherein the filter is a geotextile filter.

82. The landfill simulator of any one of clauses 78 to 81 further comprising a test sample.

83. The landfill simulator of clause 82 wherein the test sample is a bacterium for degrading plastic and wherein the waste in the waste and soil layer comprises a plastic-containing waste.

84. The landfill simulator of clause 83 wherein the plastic is a polyethylene.

85. The landfill simulator of any one of clauses 78 to 84 wherein the soil layer is the top layer, the filter is the bottom layer, the waste and soil layer and the drainage layer are between the soil layer and the filter, the waste and soil layer is between the soil layer and the drainage layer, and the drainage layer is between the filter and the waste and soil layer.

86. The landfill simulator of any one of clauses 82 to 85 for use in testing whether the test sample is capable of degrading plastic.

87. The landfill simulator of any one of clauses 82 to 86 for use in testing how rapidly the test sample is capable of degrading plastic.

88. The landfill simulator of any one of clauses 83 to 87 wherein the plastic is selected from the group consisting of a polyethylene (PE), a polyvinyl chloride (PVC), a polyurethane (PUR), a polystyrene (PS), a polyethylene terephthalate (PET), a polyolefin (PO), an epoxy resin, an elastomer, a thermoplastic, a bio-based plastic, a biodegradable plastic, and a composite plastic.

89. A method of testing whether a test sample can remove a pollutant from a landfill or control a detrimental effect of waste in the landfill, the method comprising the steps of contacting the test sample with a landfill simulator wherein the landfill simulator comprises at least four layers comprising a soil layer, a waste and soil layer, a drainage layer, and a filter.

90. The method of clause 89 wherein the soil layer is compacted soil.

91. The method of clause 89 or clause 90 wherein the drainage layer is granular.

92. The method of any one of clauses 89 to 91 wherein the filter is a geotextile filter.

93. The method of any one of clauses 89 to 92 wherein the test sample is a bacterial strain.

94. The method of clause 93 wherein the method is used to test whether the test sample can degrade a plastic and wherein the waste in the waste and soil layer comprises a plastic-containing waste.

95. The method of clause 94 wherein the plastic is a polyethylene.

96. The method of any one of clauses 89 to 95 wherein the soil layer is the top layer, the filter is the bottom layer, the waste and soil layer and the drainage layer are between the soil layer and the filter, the waste and soil layer is between the soil layer and drainage layer, and the drainage layer is between the filter and the waste and soil layer.

97. The method of any one of clauses 89 to 96 for use in testing how rapidly the test sample is capable of degrading plastic.

98. The method of any one of clauses 94 to 97 wherein the plastic is selected from the group consisting of a polyethylene (PE), a polyvinyl chloride (PVC), a polyurethane (PUR), a polystyrene (PS), a polyethylene terephthalate (PET), a polyolefin (PO), an epoxy resin, an elastomer, a thermoplastic, a bio-based plastic, a biodegradable plastic, and a composite plastic.

99. The method of any one of clauses 89 to 93 for use in testing whether the test sample is capable of reducing odor in the landfill.

100. The method of clause 99 wherein the odor is caused by $H_2S$.

101. The method of any one of clauses 1 to 14 or 22 to 25 wherein the strain is *Bacillus* strain 4954 (NRRL No. B-67474).

102. The method of clause 89 wherein the waste is a municipal solid waste mixture.

103. The method of clause 89 wherein the soil layer comprises synthetic leachate.

104. The method of clause 11 or 36 wherein the enzyme is an amylase.

105. The method of clause 11 or 36 wherein the enzyme is a xylanase.

106. The method of clause 11 or 36 wherein the enzyme is a cellulase.

107. The method of clause 11 or 36 wherein the enzyme is a protease.

108. The method of any one of clauses 1, 2, 9 to 25, 26 to 27, 34 to 50, 101, or 104 to 107 wherein the waste is a leachate from a landfill and the *Bacillus* strain can be added to the leachate from the landfill as a multiplier to increase dosage rates to the landfill when the leachate is applied back to the landfill.

109. The method of any one of clauses 1, 2, 3 to 5, 9 to 25, 26 to 30, 34 to 50, 101, or 104 to 107 wherein spores of the *Bacillus* strain are infused into the plastic.

110. The method of clause 11 or 36 wherein the enzyme is an oxioreductase.

111. The method of clause 11 or 36 wherein the enzyme is a galactosidase.

112. The method of clause 11 or 36 wherein the enzyme is an NSPase.

113. The method of clause 11 or 36 wherein the enzyme is a phytase.

114. The method of clause 11 or 36 wherein the enzyme is an arabinoxylanase.

115. The method of clause 11 or 36 wherein the enzyme is a hemicellulase.

116. The method of clause 11 or 36 wherein the enzyme is a hydrolase.

strip incubated in a control sample preparation (1A) and an HDPE strip incubated in Treatment-1 sample preparation medium (1B), where the physiology of 1B shows dark spots or cavities compared to an absence of dark spots in 1A.

Figure 2A:
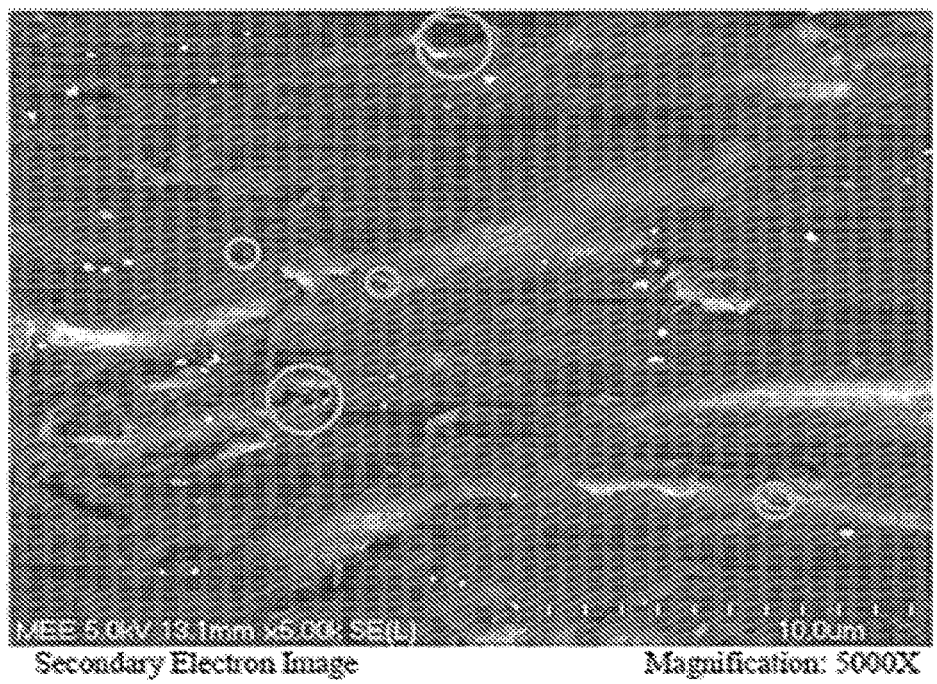
Figure 2B:
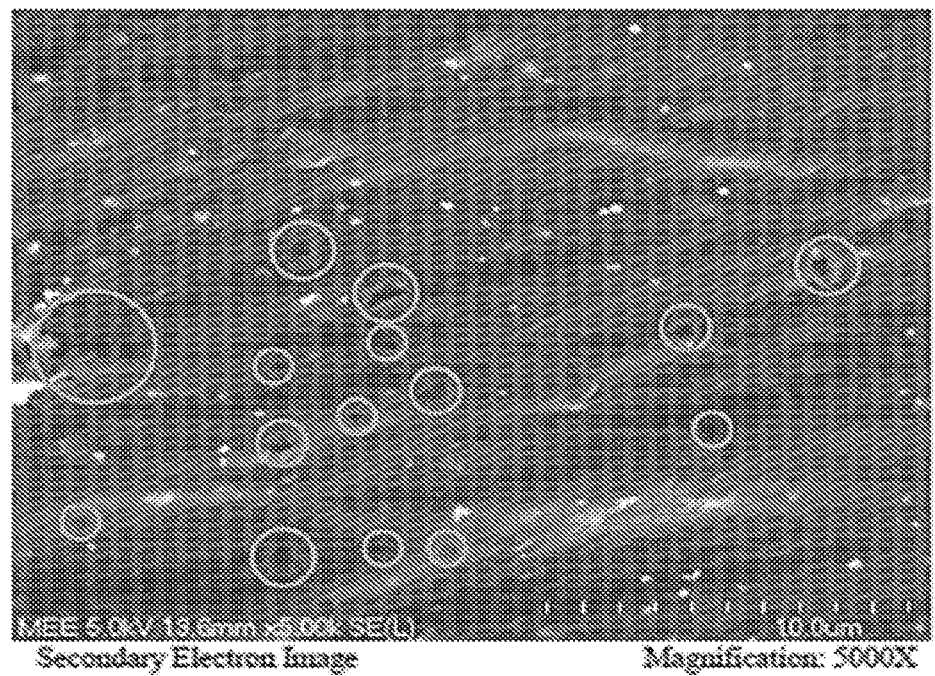

FIGS. 2A and 2B are SEM images comparing the structural physiology of an HDPE strip incubated in a control sample (2A), or an HDPE strip incubated in Treatment-2 sample preparation (2B), and both incubated in a facultative bioreactor landfill simulator, where 2B shows increased cavitation compared to the control sample in 2A.

Figure 3:
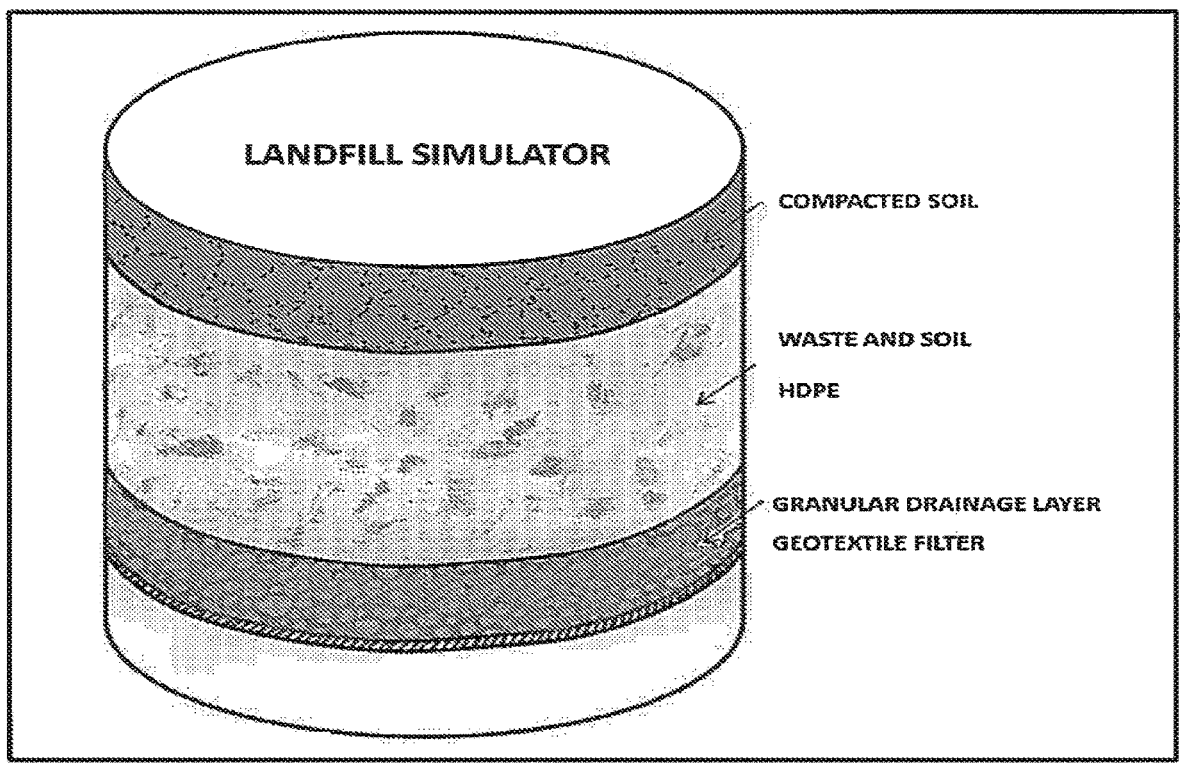

FIG. 3 is a schematic of the organization of a landfill simulator.

Figure 4A:
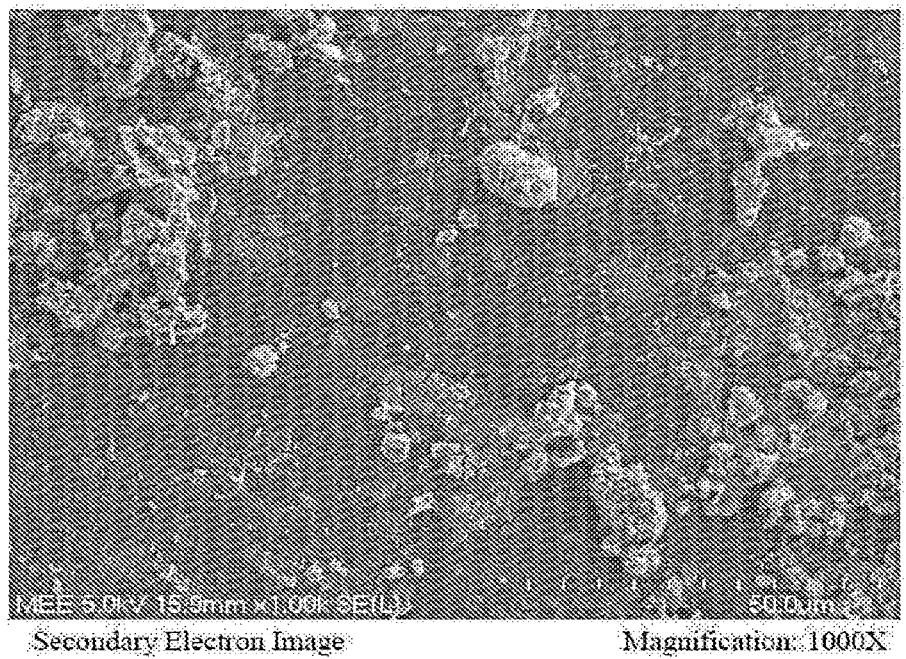
Figure 4B:
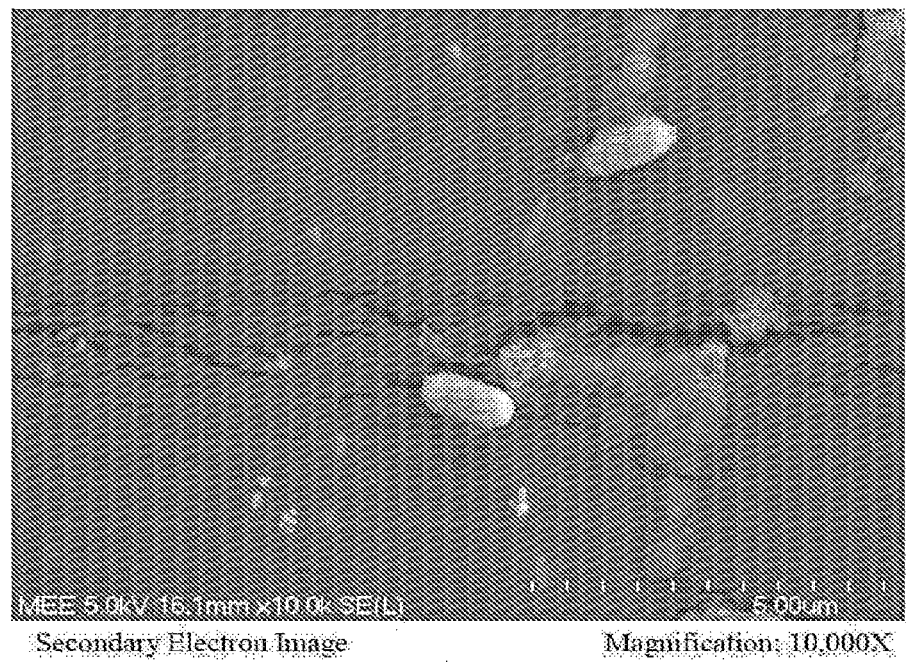
Figure 4C:
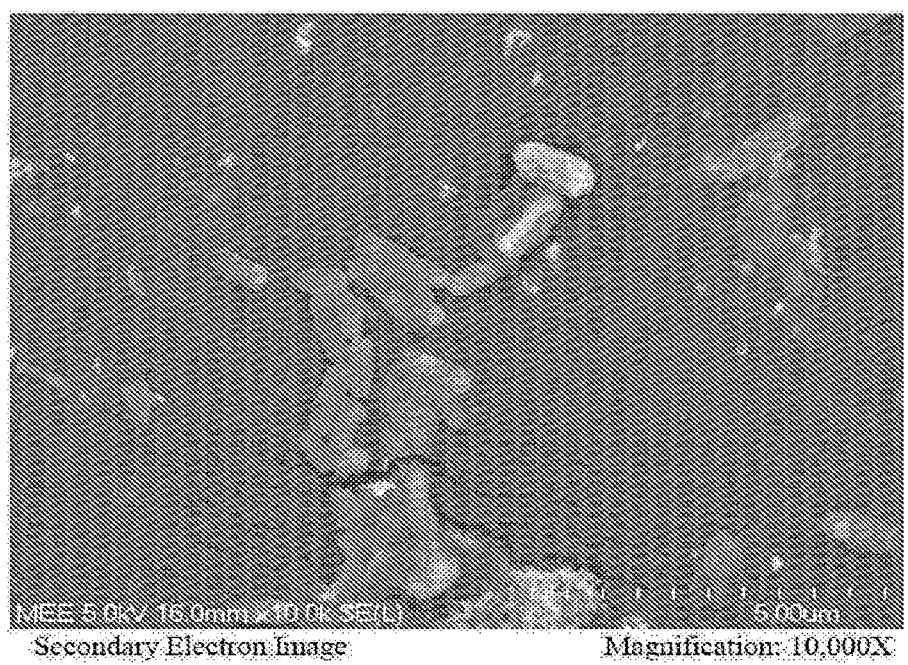

FIG. 4A-C are SEM images showing rod-shaped particles about 1-2 μm long observed in all examined areas on the HDPE film consistent with *Bacillus* microbes.

Figure 5:
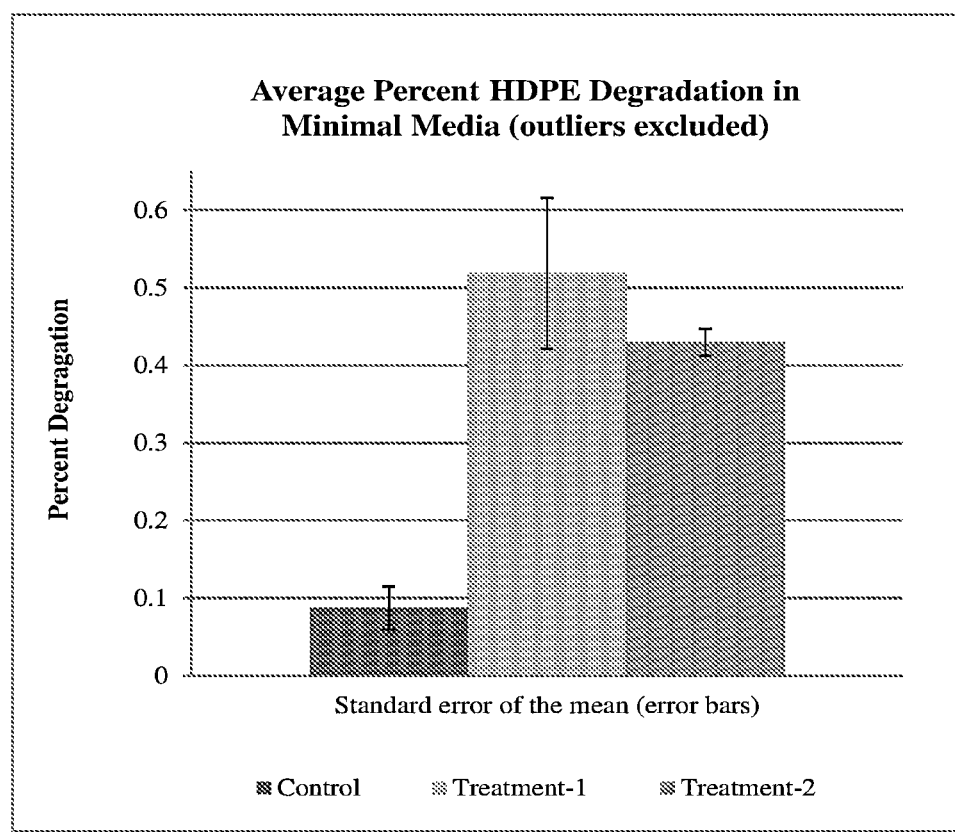

FIG. 5 shows average percent degradation of HDPE samples in minimal media for the three sample preparations (n=4, outliers excluded, p=0.0091).

Figure 6A:
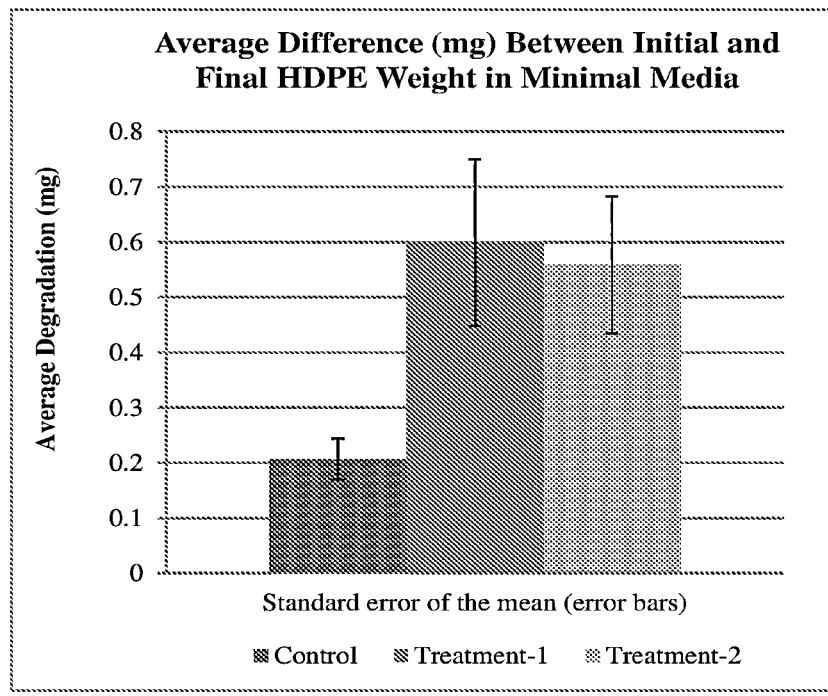
Figure 6B:
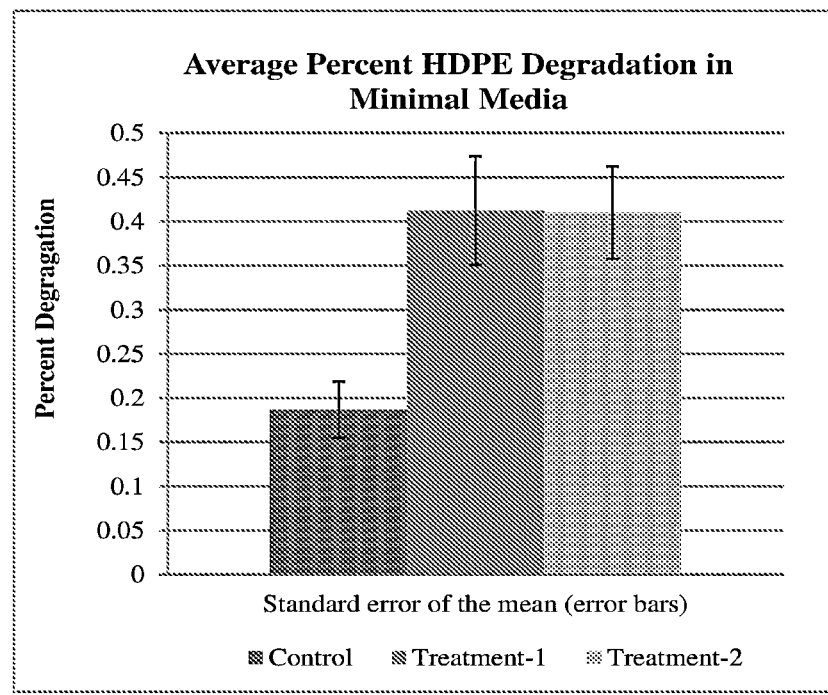

FIGS. 6A and 6B show HDPE average difference (mg) between initial and final weight in minimal medium (p=0.047) and average percent degradation of HDPE samples in minimal media for the three sample preparations (p=0.014).

Figure 7A:
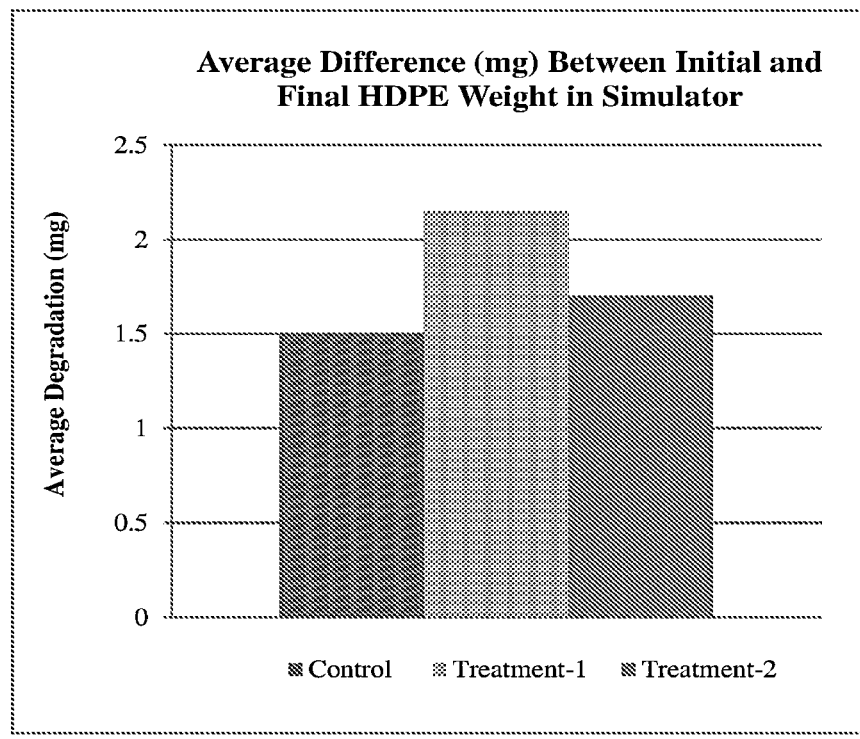
Figure 7B:
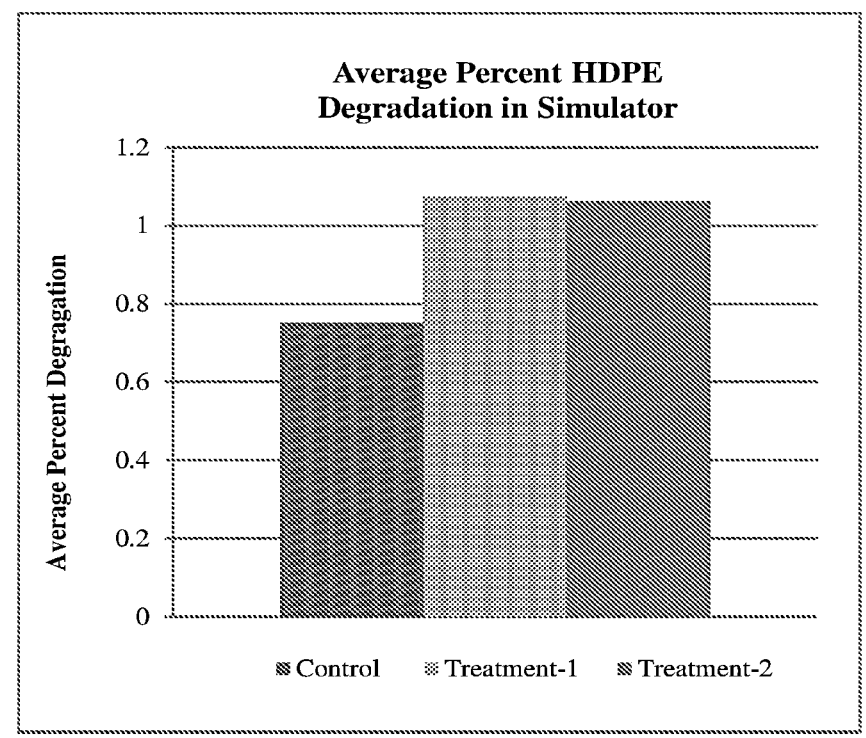

FIGS. 7A and 7B show average difference (mg) between initial and final HDPE weights in a landfill simulator and average percent degradation of HDPE in a landfill simulator.

Figure 8:
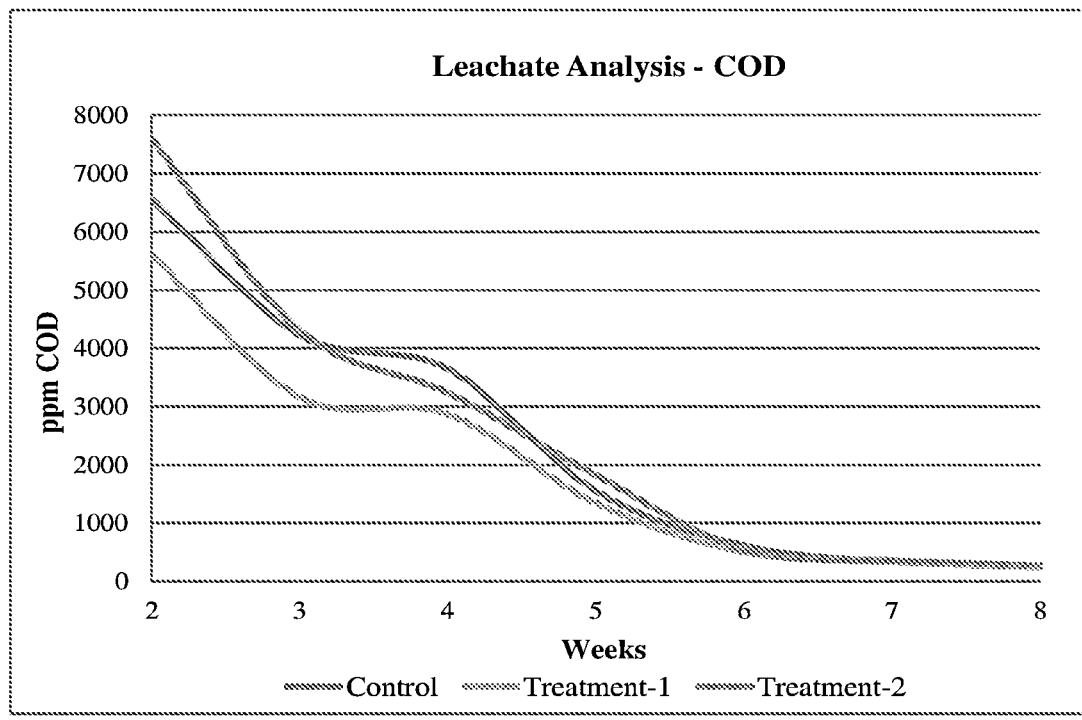

FIG. 8 shows leachate reduction of COD (weeks 2-8) following two months incubation in a simulated landfill environment.

Figure 9:
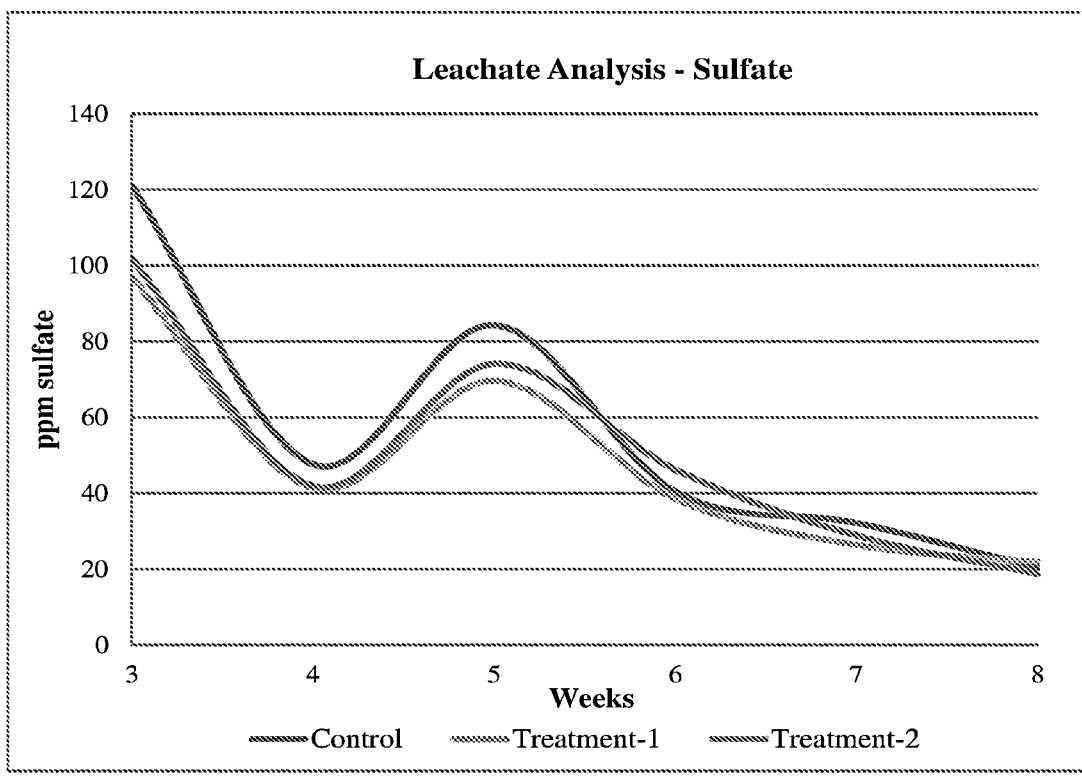

FIG. 9 shows leachate reduction of sulfate (weeks 3-8) following two months incubation in a simulated landfill environment.

Figure 10:
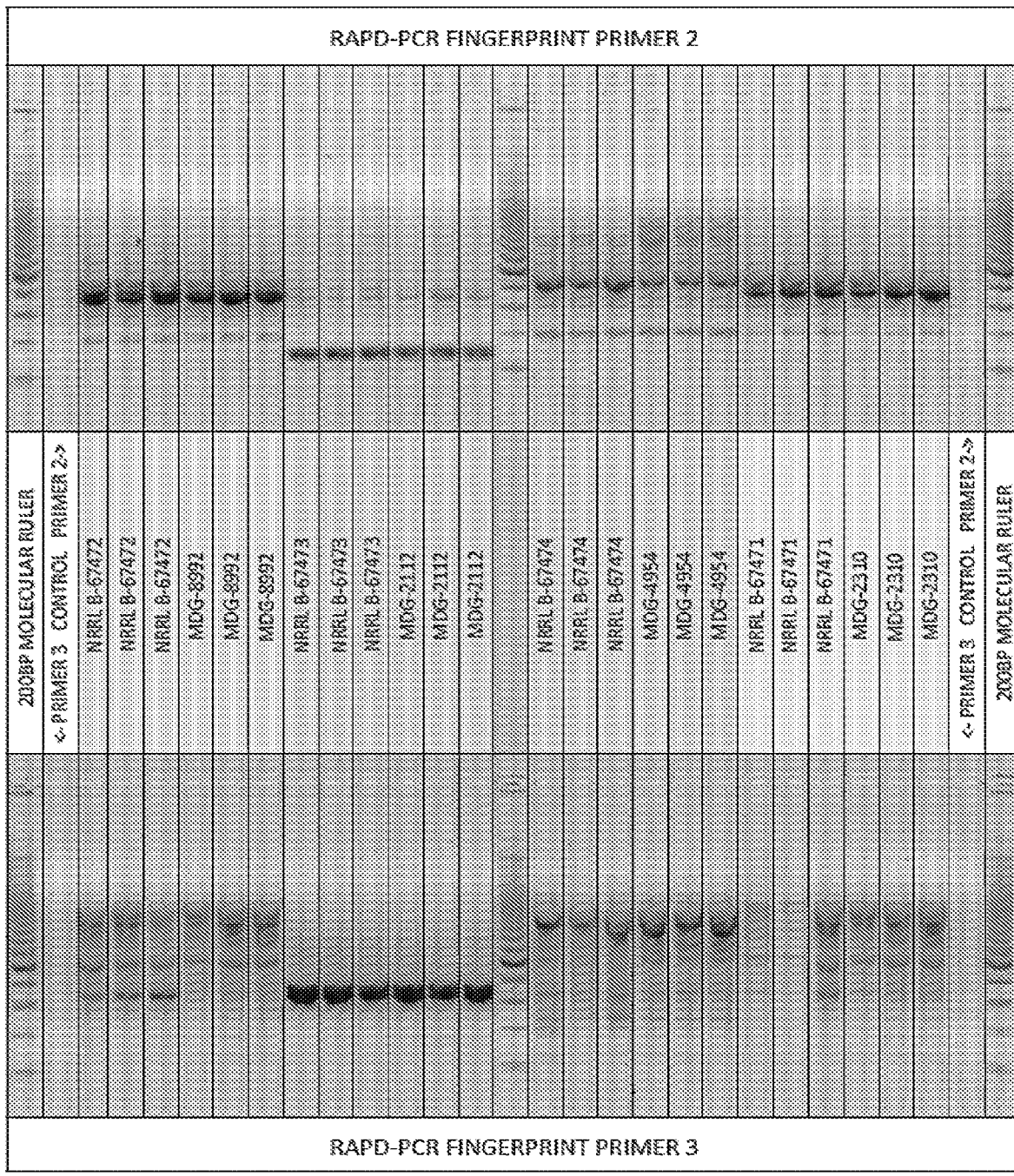

FIG. 10 shows a photograph of a gel displaying a RAPD PCR profile (Primers 2 and 3) for *Bacillus* strain 8992, *Bacillus* strain 2112, *Bacillus* strain 4954, and *Bacillus* strain 2310.

DETAILED DESCRIPTION OF ILLUSTRATIVE EMBODIMENTS

Applicants have developed *Bacillus* strains, and combinations thereof, that are useful for waste treatment, waste degradation (including plastic-containing waste) and controlling the detrimental effects of waste, such as by removing a pollutant. These strains can increase the rate of decay of plastic waste (e.g., high-density polyethylene), degrade municipal solid waste, enhance waste stabilization, reduce contaminants in waste, reduce chemical oxygen demand, reduce organics in waste (e.g., hydrocarbons), reduce odor in waste (e.g., hydrogen sulfide and sulfate), and the like. More particularly, the invention relates to isolated *Bacillus subtilis* and *Bacillus amyloliquefaciens* strains, and strains having all of the identifying characteristics of these strains, and combinations thereof, for uses comprising the above-mentioned uses. *Bacillus* strain 2112 is a *Bacillus subtilis* strain and strains 8992, 4954, and 2310 are *Bacillus amyloliquefaciens* strains.

In one embodiment a method of treating waste to remove a pollutant is provided, The method comprises contacting the waste with an effective amount of an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof, and removing the pollutant.

In another embodiment, a method of controlling a detrimental effect of waste is provided. The method comprises contacting the waste with an effective amount of an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof, and controlling the detrimental effect of the waste.

In various other embodiments, a commercial package, an additive for waste, and a composition are provided. The commercial package, additive for waste, and composition comprise an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof.

The following clauses, and combinations thereof, provide various additional illustrative aspects of the invention described herein. The various embodiments described in this section titled "DETAILED DESCRIPTION OF ILLUSTRATIVE EMBODIMENTS" are applicable to any of the following embodiments of the invention described in the numbered clauses below.

1. A method of treating waste to remove a pollutant, the method comprising contacting the waste with an effective amount of an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof, and removing the pollutant.

2. The method of clause 1 wherein the waste is selected from the group consisting of industrial waste, municipal solid waste, landfill waste, soil waste, wastewater, composting waste, contaminated groundwater, leachate from waste, polymer-containing waste, hydrocarbon-containing waste, a plastic-containing waste, a polyethylene-containing waste, a high density polyethylene-containing waste, and plastic bag-containing waste.

3. The method of clause 1 or 2 wherein the pollutant is plastic.

4. The method of any one of clauses 1 to 3 wherein the pollutant is a polyethylene.

5. The method of clause 4 wherein the pollutant is a high-density polyethylene.

6. The method of any one of clauses 1 to 5 wherein the pollutant is an organic compound.

7. The method of clause 6 wherein the organic compound is removed by degradation.

8. The method of any one of clauses 1 to 2 wherein the pollutant is an inorganic compound.

9. The method of any one of clauses 1 to 8 wherein at least one of the Bacillus strains has antimicrobial activity.

10. The method of clause 9 wherein the antimicrobial activity is against bacteria selected from the group consisting of E. coli, Salmonella, Staphylococcus, Enterococcus, Clostridia, Campylobacter, and combinations thereof.

11. The method of any one of clauses 1 to 10 wherein the Bacillus strain produces an enzyme selected from the group consisting of an a hydrolase, an oxioreductase, a galactosidase, an NSPase, a phytase, an arabinoxylanase, a cellulase, a hemicelluase, a protease, an amylase, a xylanase, an esterase, a lipase, and combinations thereof.

12. The method of clause 11 wherein the enzyme is an esterase.

13. The method of clause 11 wherein the enzyme is a lipase.

14. The method of any one of clauses 1 to 13 further comprising treating the waste with another bacterial strain selected from the group consisting of another Bacillus strain, a lactic acid bacterial strain, and combinations thereof.

15. The method of any one of clauses 1 to 14 wherein the strain is Bacillus strain 8992 (NRRL No. B-67472), or a strain having all of the identifying characteristics of Bacillus strain 8992 (NRRL No. B-67472).

16. The method of any one of clauses 1 to 14 wherein the strain is Bacillus strain 2112 (NRRL No. B-67473), or a strain having all of the identifying characteristics of Bacillus strain 2112 (NRRL No. B-67473).

17. The method of any one of clauses 1 to 14 wherein the strain is Bacillus strain 2310 (NRRL No. B-67471), or a strain having all of the identifying characteristics of Bacillus strain 2310 (NRRL No. B-67471).

18. The method of any one of clauses 1 to 14 wherein the strain is Bacillus strain 4954 (NRRL No. B-67474), or a strain having all of the identifying characteristics of Bacillus strain 4954 (NRRL No. B-67474).

19. The method of any one of clauses 1 to 14 wherein the strain is Bacillus strain 8992 (NRRL No. B-67472).

20. The method of any one of clauses 1 to 14 wherein the strain is Bacillus strain 2112 (NRRL No. B-67473).

21. The method of any one of clauses 1 to 14 wherein the strain is Bacillus strain 2310 (NRRL No. B-67471).

22. The method of any one of clauses 1 to 21 wherein the effective amount of the Bacillus strain is about $1.0 \times 10^2$ CFU/gram of the waste to about $1.0 \times 10^6$ CFU/gram of the waste.

23. The method of any one of clauses 1 to 21 wherein the effective amount of the Bacillus strain is about $1.0 \times 10^2$ CFU/gram of the waste to about $1.0 \times 10^4$ CFU/gram of the waste.

24. The method of any one of clauses 1 to 21 wherein the effective amount is an amount greater than about $1.0 \times 10^2$ CFU/gram of the waste to about $1.0 \times 10^3$ CFU/gram of the waste.

25. The method of any one of clauses 1 to 24 further comprising contacting the waste with an enzyme selected from the group consisting of a hydrolase, an oxioreductase, a galactosidase, an arabinoxylanase, a protease, a lipase, an esterase, an amylase, a hemicellulase, an arabinoxylanase, a xylanase, a cellulase, an NSPase, a phytase, and combinations thereof.

26. A method of controlling a detrimental effect of waste, the method comprising contacting the waste with an effective amount of an isolated Bacillus strain selected from the group consisting of Bacillus strain 8992 (NRRL No. B-67472), a strain having all of the identifying characteristics of Bacillus strain 8992 (NRRL No. B-67472), Bacillus strain 2112 (NRRL No. B-67473), a strain having all of the identifying characteristics of Bacillus strain 2112 (NRRL No. B-67473), Bacillus strain 4954 (NRRL No. B-67474), a strain having all of the identifying characteristics of Bacillus strain 4954 (NRRL No. B-67474), Bacillus strain 2310 (NRRL No. B-67471), a strain having all of the identifying characteristics of Bacillus strain 2310 (NRRL No. B-67471), and combinations thereof, and controlling the detrimental effect of the waste.

27. The method of clause 26 wherein the waste is selected from the group consisting of industrial waste, municipal solid waste, landfill waste, soil waste, wastewater, composting waste, contaminated groundwater, leachate from waste, polymer-containing waste, hydrocarbon-containing waste, a plastic-containing waste, a polyethylene-containing waste, a high density polyethylene-containing waste, and plastic bag-containing waste.

28. The method of clause 26 or 27 wherein the detrimental effect is caused by a plastic.

29. The method of any one of clauses 26 to 28 wherein the detrimental effect is caused by a polyethylene.

30. The method of clause 29 wherein the detrimental effect is caused by a high density polyethylene.

31. The method of any one of clauses 26 to 30 wherein the detrimental effect is caused by an organic compound.

32. The method of clause 31 wherein the organic compound is removed by degradation.

33. The method of any one of clauses 26 to 27 wherein the detrimental effect is caused by an inorganic compound.

34. The method of any one of clauses 26 to 33 wherein at least one of the Bacillus strains has antimicrobial activity.

35. The method of clause 34 wherein the antimicrobial activity is against bacteria selected from the group consisting of E. coli, Salmonella, Staphylococcus, Enterococcus, Clostridia, Campylobacter, and combinations thereof.

36. The method of any one of clauses 26 to 35 wherein the Bacillus strain produces an enzyme selected from the group consisting of a hydrolase, an oxioreductase, a galactosidase, an NSPase, a phytase, an arabinoxylanase, a cellulase, a hemicellulase, a protease, an amylase, a xylanase, an esterase, a lipase, and combinations thereof.

37. The method of clause 36 wherein the enzyme is an esterase.

38. The method of clause 36 wherein the enzyme is a lipase.

39. The method of any one of clauses 26 to 38 further comprising treating the waste with another bacterial strain selected from the group consisting of another Bacillus strain, a lactic acid bacterial strain, and combinations thereof.

40. The method of any one of clauses 26 to 39 wherein the strain is Bacillus strain 8992 (NRRL No. B-67472), or a strain having all of the identifying characteristics of Bacillus strain 8992 (NRRL No. B-67472).

41. The method of any one of clauses 26 to 39 wherein the strain is Bacillus strain 2112 (NRRL No. B-67473), or a strain having all of the identifying characteristics of Bacillus strain 2112 (NRRL No. B-67473).

42. The method of any one of clauses 26 to 39 wherein the strain is *Bacillus* strain 2310 (NRRL No. B-67471), or a strain having all of the identifying characteristics of *Bacillus* strain 2310 (NRRL No. B-67471).

43. The method of any one of clauses 26 to 39 wherein the strain is *Bacillus* strain 4954 (NRRL No. B-67474), or a strain having all of the identifying characteristics of *Bacillus* strain 4954 (NRRL No. B-67474).

44. The method of any one of clauses 26 to 39 wherein the strain is *Bacillus* strain 8992 (NRRL No. B-67472).

45. The method of any one of clauses 26 to 39 wherein the strain is *Bacillus* strain 2112 (NRRL No. B-67473).

46. The method of any one of clauses 26 to 39 wherein the strain is *Bacillus* strain 2310 (NRRL No. B-67471).

47. The method of any one of clauses 26 to 39 wherein the strain is *Bacillus* strain 4954 (NRRL No. B-67474).

48. The method of any one of clauses 26 to 47 wherein the effective amount of the *Bacillus* strain is about $1.0 \times 10^2$ CFU/gram of the waste to about $1.0 \times 10^6$ CFU/gram of the waste.

49. The method of any one of clauses 26 to 47 wherein the effective amount of the *Bacillus* strain is about $1.0 \times 10^2$ CFU/gram of the waste to about $1.0 \times 10^3$ CFU/gram of the waste.

50. The method of any one of clauses 26 to 49 further comprising contacting the waste with an enzyme selected from the group consisting of a hydrolase, an oxioreductase, a galactosidase, an NSPase, a phytase, an arabinoxylanase, a cellulase, a hemicellulase, a protease, an amylase, a xylanase, an esterase, a lipase, and combinations thereof.

51. A commercial package comprising an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof.

52. An additive for waste comprising an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof.

53. A composition comprising an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof.

54. The commercial package, additive, or composition of any one of clauses 51 to 53 wherein the *Bacillus* strain causes degradation of an organic compound or removal of an inorganic compound in waste.

55. The commercial package, additive, or composition of any one of clauses 51 54 wherein the *Bacillus* strain is in the form of a concentrate.

56. The commercial package, additive, or composition of any one of clauses 51 to 54 wherein the *Bacillus* strain is in the form of a superconcentrate.

57. The commercial package, additive, or composition of any one of clauses 51 to 56 wherein the *Bacillus* strain is in dry form.

58. The commercial package, additive, or composition of any one of clauses 51 to 57 wherein the *Bacillus* strain is in pelleted form.

59. The commercial package, additive, or composition of any one of clauses 51 to 56 wherein the strain is in a form selected from the group consisting of a powder, a liquid, and a pellet form.

60. The commercial package, additive, or composition of any one of clauses 51 to 59 further comprising a carrier for the *Bacillus* strain.

61. The commercial package, additive, or composition of clause 60 wherein the carrier is selected from the group consisting of salt, a dextrin, and combinations thereof.

62. The commercial package, additive, or composition of any one of clauses 51 to 61 in a bag.

63. The commercial package, additive, or composition of clause 62 wherein the bag is a plastic bag.

64. The commercial package, additive, or composition of any one of clauses 51 to 63 further comprising instructions for use of one or more of the *Bacillus* strains.

65. The commercial package, additive, or composition of any one of clauses 51 to 64 in a 20-pound bag.

66. The commercial package, additive, or composition of any one of clauses 51 to 64 in a 50-pound bag.

67. The commercial package, additive, or composition of any one of clauses 51 to 57 or 60 to 66 wherein the *Bacillus* strain is in powder form.

68. The commercial package, additive, or composition of any one of clauses 51 to 56 wherein the *Bacillus* strain is in liquid form.

69. The commercial package, additive, or composition of any one of clauses 51 to 68 wherein the *Bacillus* strain is in a container for commercial use.

70. The commercial package, additive, or composition of clause 69 wherein the container comprises plastic.

71. The commercial package, additive, or composition of clause 69 wherein the container comprises paper.

72. The commercial package, additive, or composition of any one of clauses 51 to 71 further comprising a binder.

73. The commercial package, additive, or composition of clause 72 wherein the binder is selected from the group consisting of clay, yeast cell wall components, aluminum silicate, and glucan, or combinations thereof.

74. The commercial package, additive, or composition of any one of clauses 51 to 73 wherein the *Bacillus* strain degrades a plastic.

75. The commercial package, additive, or composition of any one of clauses 51 to 74 wherein the *Bacillus* strain degrades a high density polyethylene.

76. The method of any one of clauses 26 to 50 wherein the detrimental effect is odor and the odor is controlled.

77. The method of clause 76 wherein the odor is caused by sulfate and hydrogen sulfide ($H_2S$) production.

78. A landfill simulator comprising at least four layers comprising a soil layer, a waste and soil layer, a drainage layer, and a filter.

79. The landfill simulator of clause 78 wherein the soil layer is compacted soil.

80. The landfill simulator of clause 78 or clause 79 wherein the drainage layer is granular.

81. The landfill simulator of any one of clauses 78 to 80 wherein the filter is a geotextile filter.

82. The landfill simulator of any one of clauses 78 to 81 further comprising a test sample.

83. The landfill simulator of clause 82 wherein the test sample is a bacterium for degrading plastic and wherein the waste in the waste and soil layer comprises a plastic-containing waste.

84. The landfill simulator of clause 83 wherein the plastic is a polyethylene.

85. The landfill simulator of any one of clauses 78 to 84 wherein the soil layer is the top layer, the filter is the bottom layer, the waste and soil layer and the drainage layer are between the soil layer and the filter, the waste and soil layer is between the soil layer and the drainage layer, and the drainage layer is between the filter and the waste and soil layer.

86. The landfill simulator of any one of clauses 82 to 85 for use in testing whether the test sample is capable of degrading plastic.

87. The landfill simulator of any one of clauses 82 to 86 for use in testing how rapidly the test sample is capable of degrading plastic.

88. The landfill simulator of any one of clauses 83 to 87 wherein the plastic is selected from the group consisting of a polyethylene (PE), a polyvinyl chloride (PVC), a polyurethane (PUR), a polystyrene (PS), a polyethylene terephthalate (PET), a polyolefin (PO), an epoxy resin, an elastomer, a thermoplastic, a bio-based plastic, a biodegradable plastic, and a composite plastic.

89. A method of testing whether a test sample can remove a pollutant from a landfill or control a detrimental effect of waste in the landfill, the method comprising the steps of contacting the test sample with a landfill simulator wherein the landfill simulator comprises at least four layers comprising a soil layer, a waste and soil layer, a drainage layer, and a filter.

90. The method of clause 89 wherein the soil layer is compacted soil.

91. The method of clause 89 or clause 90 wherein the drainage layer is granular.

92. The method of any one of clauses 89 to 91 wherein the filter is a geotextile filter.

93. The method of any one of clauses 89 to 92 wherein the test sample is a bacterial strain.

94. The method of clause 93 wherein the method is used to test whether the test sample can degrade a plastic and wherein the waste in the waste and soil layer comprises a plastic-containing waste.

95. The method of clause 94 wherein the plastic is a polyethylene.

96. The method of any one of clauses 89 to 95 wherein the soil layer is the top layer, the filter is the bottom layer, the waste and soil layer and the drainage layer are between the soil layer and the filter, the waste and soil layer is between the soil layer and drainage layer, and the drainage layer is between the filter and the waste and soil layer.

97. The method of any one of clauses 89 to 96 for use in testing how rapidly the test sample is capable of degrading plastic.

98. The method of any one of clauses 94 to 97 wherein the plastic is selected from the group consisting of a polyethylene (PE), a polyvinyl chloride (PVC), a polyurethane (PUR), a polystyrene (PS), a polyethylene terephthalate (PET), a polyolefin (PO), an epoxy resin, an elastomer, a thermoplastic, a bio-based plastic, a biodegradable plastic, and a composite plastic.

99. The method of any one of clauses 89 to 93 for use in testing whether the test sample is capable of reducing odor in the landfill.

100. The method of clause 99 wherein the odor is caused by $H_2S$.

101. The method of any one of clauses 1 to 14 or 22 to 25 wherein the strain is *Bacillus* strain 4954 (NRRL No. B-67474).

102. The method of clause 89 wherein the waste is a municipal solid waste mixture.

103. The method of clause 89 wherein the soil layer comprises synthetic leachate.

104. The method of clause 11 or 36 wherein the enzyme is an amylase.

105. The method of clause 11 or 36 wherein the enzyme is a xylanase.

106. The method of clause 11 or 36 wherein the enzyme is a cellulase.

107. The method of clause 11 or 36 wherein the enzyme is a protease.

108. The method of any one of clauses 1, 2, 9 to 25, 26 to 27, 34 to 50, 101, or 104 to 107 wherein the waste is a leachate from a landfill and the *Bacillus* strain can be added to the leachate from the landfill as a multiplier to increase dosage rates to the landfill when the leachate is applied back to the landfill.

109. The method of any one of clauses 1, 2, 3 to 5, 9 to 25, 26 to 30, 34 to 50, 101, or 104 to 107 wherein spores of the *Bacillus* strain are infused into the plastic.

110. The method of clause 11 or 36 wherein the enzyme is an oxioreductase.

111. The method of clause 11 or 36 wherein the enzyme is a galactosidase.

112. The method of clause 11 or 36 wherein the enzyme is an NSPase.

113. The method of clause 11 or 36 wherein the enzyme is a phytase.

114. The method of clause 11 or 36 wherein the enzyme is an arabinoxylanase.

115. The method of clause 11 or 36 wherein the enzyme is a hemicellulase.

116. The method of clause 11 or 36 wherein the enzyme is a hydrolase.

In various embodiments, the *Bacillus* strain (e.g., *Bacillus* strain 8992 (NRRL No. B-67472), *Bacillus* strain 2112 (NRRL No. B-67473), *Bacillus* strain 4954 (NRRL No. B-67474), or *Bacillus* strain 2310 (NRRL No. B-67471) for use in accordance with the methods, commercial packages, additives for waste, and compositions described herein can be selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof. *Bacillus* strains 8992 2112, 4954, and 2310 were deposited on Jun. 27, 2017 at the Agricultural Research Service Culture Collection (NRRL), International Depository Authority, 1815 North University Street, Peoria, Illinois 61604-3999, and were given accession numbers NRRL No. B-67472, NRRL No. B-67473, NRRL No. B-67474, and NRRL No. B-67471, respectively. The deposits were made under the provisions of the Budapest Treaty on the International Recognition of the Deposit of Microorganisms for the Purposes of Patent Procedure. The NRRL strain designations are MDG-8992, MDG-2112, MDG-4954, and MDG-2310, which are equivalent to Bacillus strain 8992, 2112, 4954, and 2310, respectively, as referred to in the application.

Any of these strains can be used to treat waste alone or in combination in the form of an additive for waste or a composition as described herein (e.g., an additive or a composition further comprising a carrier and/or a binder). In one embodiment, multiple strains are used to treat waste in combination in a single composition. In another embodiment, multiple strains are used to treat waste in combination in separate compositions.

As used herein "a strain having all of the identifying characteristics of" Bacillus strain 8992, 2112, 4954, or 2310 can be a mutant strain having all of the identifying characteristics of Bacillus strain 8992, 2112, 4954, or 2310 (e.g., a DNA fingerprint based on DNA analysis that corresponds to the DNA fingerprint of Bacillus strain 8992, 2112, 4954, or 2310, enzyme activities that correspond to Bacillus strain 8992, 2112, 4954, or 2310, antimicrobial activity that corresponds to Bacillus strain 8992, 2112, 4954, or 2310, antibiotic sensitivity and tolerance profiles that correspond to Bacillus strain 8992, 2112, 4954, or 2310, or combinations thereof). In alternate embodiments, the mutation can be a natural mutation, or a genetically engineered mutation. In another embodiment, "a strain having all of the identifying characteristics of" Bacillus strain 8992, 2112, 4954, or 2310 can be a strain, for example, produced by isolating one or more plasmids from Bacillus strain 8992, 2112, 4954, or 2310 and introducing the one or more plasmids into another bacterium, such as another Bacillus strain, as long as the one or more plasmids contain DNA that provides the identifying characteristics of Bacillus strain 8992, 2112, 4954, or 2310 (e.g., a DNA fingerprint based on DNA analysis that corresponds to the DNA fingerprint of Bacillus strain 8992, 2112, 4954, or 2310).

In another embodiment, one or more of the Bacillus strains described in the preceding paragraphs (e.g., Bacillus strain 8992, 2112, 4954, or 2310) can be used to treat waste along with another bacterial strain selected from the group consisting of another Bacillus strain, a lactic acid bacterial strain, and combinations thereof. In still another embodiment, the additional Bacillus strain can be selected from the group consisting of Bacillus subtilis, Bacillus amyloliquefaciens, Bacillus licheniformis, Bacillus pumilus, Bacillus mojavensis, Bacillus methylotrophicus, other Bacillus strains, and combinations thereof. In yet another embodiment, one or more of the Bacillus strains described in the preceding paragraphs (e.g., Bacillus strain 8992, 2112, 4954, or 2310) can be used to treat waste along with any other bacterial strain effective to treat waste to remove pollutants or to control detrimental effects of waste.

The additive for waste or the composition described herein can be used to treat waste for any period of time that is effective to remove pollutants and/or control the detrimental effects of waste. For example, in one embodiment treatment of waste can occur daily. The time periods for treatment of waste are non-limiting and it should be appreciated that any time period or treatment schedule determined to be effective to remove pollutants and/or control the detrimental effects of waste may be used.

In various illustrative embodiments, the Bacillus strain (e.g., Bacillus strain 8992, 2112, 4954, and/or 2310), or any other bacterial strains added in addition to Bacillus strain 8992, 2112, 4954, and/or 2310, can be added to the waste at about $1.0 \times 10^2$ CFU/gram of the waste, about $1.0 \times 10^2$ CFU/gram of the waste to about $1.0 \times 10^3$ CFU/gram of the waste, about $1.0 \times 10^2$ CFU/gram of the waste to about $1.0 \times 10^4$ CFU/gram of the waste, about $1.0 \times 10^2$ CFU/gram of the waste to about $1.0 \times 10^5$ CFU/gram of the waste, about $1.0 \times 10^2$ CFU/gram of the waste to about $1.0 \times 10^6$ CFU/gram of the waste, about $1.0 \times 10^3$ CFU/gram of the waste to about $5.0 \times 10^{12}$ CFU/gram of the waste or at about $1.0 \times 10^3$ CFU/gram of the waste to about $1.0 \times 10^{10}$ CFU/gram of the waste. In other embodiments, the Bacillus strain (e.g., Bacillus strain 8992, 2112, 4954, and/or 2310) can be added to the waste at an amount greater than about $1.0 \times 10^2$ CFU/gram of the waste, at greater than about $1.0 \times 10^3$ CFU/gram of the waste, at greater than about $1.1 \times 10^3$ CFU/gram of the waste, at greater than about $1.25 \times 10^3$ CFU/gram of the waste, at greater than about $1.5 \times 10^3$ CFU/pound of the waste, at greater than about $1.75 \times 10^3$ CFU/gram of the waste, at greater than about $1.0 \times 10^4$ CFU/gram of the waste, at greater than about $2.0 \times 10^4$ CFU/gram of the waste, at greater than about $3.0 \times 10^4$ CFU/gram of the waste, at greater than about $4.0 \times 10^4$ CFU/gram of the waste, at greater than about $5.0 \times 10^4$ CFU/gram of the waste, at greater than about $6.0 \times 10^4$ CFU/gram of the waste, at greater than about $7.0 \times 10^4$ CFU/gram of the waste, at greater than about $8.0 \times 10^4$ CFU/gram of the waste, at greater than about $1.0 \times 10^5$ CFU/gram of the waste, at greater than about $1.0 \times 10^6$ CFU/gram of the waste, at greater than about $1.0 \times 10^7$ CFU/gram of the waste, at greater than about $1.0 \times 10^8$ CFU/gram of the waste, at greater than about $1.0 \times 10^9$ CFU/gram of the waste, at greater than about $1.0 \times 10^{10}$ CFU/gram of the waste, at greater than about $1.0 \times 10^{11}$ CFU/gram of the waste, or at greater than about $1.0 \times 10^{12}$ CFU/gram of the waste.

In various embodiments, the waste described herein can be selected from the group consisting of industrial waste, municipal solid waste, landfill waste, soil waste, wastewater, composting waste, contaminated groundwater, leachate from waste, polymer-containing waste, hydrocarbon-containing waste, a plastic-containing waste, a polyethylene-containing waste, a high density polyethylene-containing waste, and plastic bag-containing waste. In another embodiment, the plastic-containing waste can be a polyethylene-containing waste (e.g., a high-density polyethylene), or any other type of waste comprising pollutants that need to be removed or having a detrimental effect that needs to be controlled. In another embodiment, the plastic-containing waste can be selected from the group consisting of a polyethylene (PE), a polyvinyl chloride (PVC), a polyurethane (PUR), a polystyrene (PS), a polyethylene terephthalate (PET), a polyolefin (PO), an epoxy resin, an elastomer, a thermoplastic, a bio-based plastic, a biodegradable plastic, and a composite plastic.

In another embodiment where the waste is leachate from a landfill, the Bacillus strain can be added to the leachate from a landfill as a multiplier to increase dosage rates to the landfill when the leachate is applied back to the landfill (i.e., the strains multiply in the leachate so the dose that is applied back to the landfill is increased). In yet another embodiment spores from the Bacillus strain can be infused into plastic (e.g., plastic bag-containing waste and plastic-containing waste) to treat the plastic with the *Bacillus* strain.

As used herein "remove a pollutant" or "removal of a pollutant" means completely removing the pollutant, reducing the amount of the pollutant, inactivating the pollutant, degrading the pollutant, or causing the pollutant to be converted to an inactivated form. As used herein "controlling a detrimental effect of waste" or similar phrases means completely removing a pollutant causing the detrimental effect, reducing the amount of the pollutant causing the detrimental effect, inactivating the pollutant causing the detrimental effect, degrading the pollutant causing the detrimental effect, or causing the pollutant responsible for the detrimental effect to be converted to an inactivated form. "Controlling a detrimental effect of waste" can mean degrading waste, enhancing waste stabilization, reducing contaminants in waste, reducing COD, reducing organics in waste (e.g., hydrocarbons), reducing odor in waste (e.g., $H_2S$ and sulfate), and the like.

In various illustrative aspects, the pollutants that can be removed from the waste can be selected from the group consisting of a harmful microorganism, an organic compound, an inorganic compound, a plastic-containing compound, a polyethelene-containing compound, a high-density polyethelene-containing compound, and combinations thereof, and the like. In some embodiments described herein, at least one of the *Bacillus* strains can have antimicrobial activity. Such antimicrobial activity can be against, for example, *E. coli, Salmonella, Staphylococcus, Enterococcus, Clostridia, Campylobacter*, and combinations thereof.

In the embodiment where the pollutant is an organic compound, the organic compound can be removed by degradation. In this embodiment, the organic compound can be, for example, a plastic-containing compound, a polyethelene-containing compound, a high-density polyethelene-containing compound, and combinations thereof, and the like, or a by-product of any other organic compound that is a pollutant in waste or is the cause of a detrimental effect of waste. In the embodiment where the pollutant is an organic compound, the organic compound can be from, for example, a grocery bag, or any other waste that is plastic-containing waste, including a polyethelene-containing waste or a high-density polyethelene-containing waste.

In various illustrative aspects, the *Bacillus* strains described herein (i.e., *Bacillus* strains 8992, 2112, 4954, and/or 2310) produce an enzyme selected from the group consisting of a hydrolase, an oxioreductase, a galactosidase, an NSPase, a phytase, an arabinoxylanase, a cellulase, a hemicellulase, a protease, an amylase, a xylanase, an esterase, a lipase, and combinations thereof.

In one illustrative embodiment, one or more enzymes may be added to the additive for waste or the composition described herein or may be added directly to the waste in combination with the *Bacillus* strains described herein. In various embodiments, the enzymes that may be used to treat the waste in addition to the *Bacillus* strains include a hydrolase, an oxioreductase, a galactosidase, an NSPase, a phytase, an arabinoxylanase, a cellulase, a hemicellulase, a protease, an amylase, a xylanase, an esterase, a lipase, and combinations thereof, and any other enzyme that is suitable to treat waste to remove pollutants or control a detrimental effect of waste. Any of the enzymes described above that are suitable for treatment of waste may be added as a component of the commercial package, additive for waste, or composition described herein, or may be added directly the waste as a separate composition.

In additional embodiments of the invention, compositions comprising *Bacillus* strain 8992, 2112, 4954, and/or 2310 are provided. In one embodiment, a commercial package is provided comprising an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof.

In another embodiment, an additive for waste is provided comprising an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof.

In yet another embodiment, a composition is provided comprising an isolated *Bacillus* strain selected from the group consisting of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), a strain having all of the identifying characteristics of *Bacillus* strain 2310 (NRRL No. B-67471), and combinations thereof.

In these embodiments the *Bacillus* strain can be in the form of, for example, a powder, a liquid, or pellets, and can be mixed with the waste using any suitable method known in the art to achieve any of the amounts of *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), or a strain having all of the identifying characteristics of *Bacillus* strain 2310 (NRRL No. B-67471), and combinations thereof, for the treatment of waste to remove pollutants or to control a detrimental effect of waste.

In any of the composition embodiments described herein, the *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), or a strain having all of the identifying characteristics of *Bacillus* strain 2310 (NRRL No. B-67471), and combinations thereof, can inhibit a pathogen selected from the group consisting of *E. coli, Salmonella, Staphylococcus, Enterococcus, Clostridia, Campylobacter*, and combinations thereof. These types of microorganisms are non-limiting examples of the types of microorganisms the *Bacillus* strains can inhibit.

In these embodiments, the *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), or a strain having all of the identifying characteristics of *Bacillus* strain 2310 (NRRL No. B-67471), and combinations thereof, can cause degradation or removal of an organic compound or removal of an inorganic compound in waste.

In illustrative aspects, the *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of the identifying characteristics of *Bacillus* strain 4954 (NRRL No. B-67474), *Bacillus* strain 2310 (NRRL No. B-67471), or a strain having all of the identifying characteristics of *Bacillus* strain 2310 (NRRL No. B-67471), and combinations thereof, can be in the form of a commercial package, an additive for waste or any suitable composition. In another illustrative embodiment, the *Bacillus* strain(s) in the commercial package, additive for waste, or composition can be in the form of a concentrate (e.g., about $1 \times 10^8$ to about $5 \times 10^9$ CFU/g) or a superconcentrate (e.g., about $1 \times 10^{10}$ to about $5 \times 10^{12}$ CFU/g). In another embodiment, the *Bacillus* strain(s) in the commercial package, additive for waste, or composition can be in a dry form (e.g., a powder), a pelleted form, a liquid form, a freeze-dried form, or in the form of a gel, or any other suitable form.

In another illustrative embodiment, the *Bacillus* strain(s) in the commercial package, additive for waste, or composition can further comprise a carrier for the *Bacillus* strain(s). In various embodiments, the carrier can be selected from the group consisting of a salt, mineral oil, a dextrin (e.g., maltodextrin), whey, sugar, limestone, dried starch, sodium silico aluminate, and combinations thereof. In another embodiment, the carrier can be any suitable carrier known in the art for a composition for treating waste. In another embodiment, the *Bacillus* strain(s) in the commercial package, additive for waste, or composition can further comprise a binder such as clay, yeast cell wall components, aluminum silicate, glucan, or other known binders, and/or micronutrients, including but not limited to, nitrogen and phosphorus.

In yet other embodiments, the commercial package, additive for waste, or composition comprising *Bacillus* strain 8992 (NRRL No. B-67472), a strain having all of the identifying characteristics of *Bacillus* strain 8992 (NRRL No. B-67472), *Bacillus* strain 2112 (NRRL No. B-67473), a strain having all of the identifying characteristics of *Bacillus* strain 2112 (NRRL No. B-67473), *Bacillus* strain 4954 (NRRL No. B-67474), a strain having all of 2310 (NRRL No. B-67471), or a strain having all of the identifying characteristics of *Bacillus* strain 2310 (NRRL No. B-67471), and combinations thereof, is in a container for commercial use. In various embodiments the container can be, for example, a bag (e.g., a 20-pound bag, a bag, a 2-ounce bag, a 1-pound bag, or a 1-kilogram bag), a pouch, a drum, a bottle, or a box. In illustrative aspects, the container comprising the *Bacillus* strain(s) can comprise plastic, metal, foil, paper, fiber, or cardboard (e.g., a plastic pail, a paper bag, a foil bag, a fiber drum, etc.). The commercial package can further comprise instructions for use of one or more of the *Bacillus* strains.

In other illustrative embodiments, a landfill simulator of clauses or claims 78 to 88 or the method of using a landfill simulator of clauses or claims 89 to 100 can be used to test whether a test sample can remove a pollutant from a landfill or control a detrimental effect of waste in the landfill, the method comprising the steps of contacting the test sample with a landfill simulator wherein the landfill simulator comprises at least four layers comprising a soil layer, a waste and soil layer, a drainage layer, and a filter. A diagram of an exemplary landfill simulator is shown in FIG. 3.

The following examples are for illustrative purposes only. The examples are non-limiting, and are not intended to limit the invention in any way.

Example 1

HDPE in Minimal Media Preparation

Lab-scale testing was conducted twice in minimal media containing pre-weighed high-density polyethylene (HDPE) as a sole carbon source. Three preparations were made in quadruplicate—a control containing only the minimal media, micronutrients, and HDPE; Treatment-1 (analogous to COMBO-1 in the priority document) including the minimal media, MDG-8992, MDG-2112, micronutrients and HDPE; and Treatment-2 (analogous to COMBO-2 in the priority document) including the minimal media, MDG-4954, MDG-2310, micronutrients and HDPE. Inoculation and media replacement occurred weekly over two months (pH=7.0 at increasing the rate of decay of HDPE.

Post incubation, HDPE strips were soaked in a 2% sodium dodecyl sulfate (SDS) solution and washed with deionized water to remove biofilm and contaminants. The HDPE film was dried at 55° C. for 72 hours and weighed using a Mettler Toledo Analytical Balance (model number XS104; obtained from Mettler Toledo). Results for the initial minimal medium experiment were calculated excluding and including outliers (n=4). The microbial degradation of HDPE was analyzed by measuring the dry-weight reduction of HDPE film showing statistical significance of treatment using one-way analysis of variance (ANOVA) and scanning electron microscopy (SEM). Results from combined initial and duplicate experiments including outliers (n=8) were also assessed by measuring the dry-weight reduction of HDPE film and one-way ANOVA to determine significance.

Example 2

Results and Analysis From HDPE Experiment In Minimal Media Preparation

The following calculation was used to calculate the dry-weight reduction of HDPE samples: % mass loss=[(initial weight minus final weight)/initial weight]×100. Results were analyzed with and without outliers. Outliers were determined using the Iglewicz and Hoaglin outlier test (1993), "Volume 16: How to Detect and Handle Outliers", The ASQC Basic References in Quality Control: Statistical Techniques, Edward F. Mykytka, Ph.D., Editor. Results for the initial minimal media experiment excluding outliers (n=4) show degradation at 0.09%±0.05, 0.52%±0.19 and 0.43%±0.04 for control, treatment-1, and treatment-2 respectively (FIG. 5). Assuming a simple linear rate of degradation, the projected time for HDPE materials to degrade completely was 171 years, 30 years and 36 years for Control, Treatment-1 and Treatment-2 preparations, respectively (Table 1).

TABLE 1

Projected time to complete degradation given constant rate.

| Sample | % Average | Years to Degrade |
| --- | --- | --- |
| Control | 0.09 | 171 |
| Treatment-1 | 0.52 | 30 |
| Treatment-2 | 0.43 | 36 |

Statistical significance of treatment on the difference between initial and final HDPE weights was calculated using one-way ANOVA. When the p-value is lower than 0.05, one or more treatments are significantly different. One-way ANOVA for percent degradation of HDPE excluding outliers had a p-value at p=0.0091 and f-statistic at f=9.9180. One-way ANOVA for the milligram difference between initial and final weights including outliers had p=0.004. One-way ANOVA fit to a general linear model (GLM) for the milligram difference between initial and final weights using initial weight as a covariate had p=0.006.

Figure 1A:
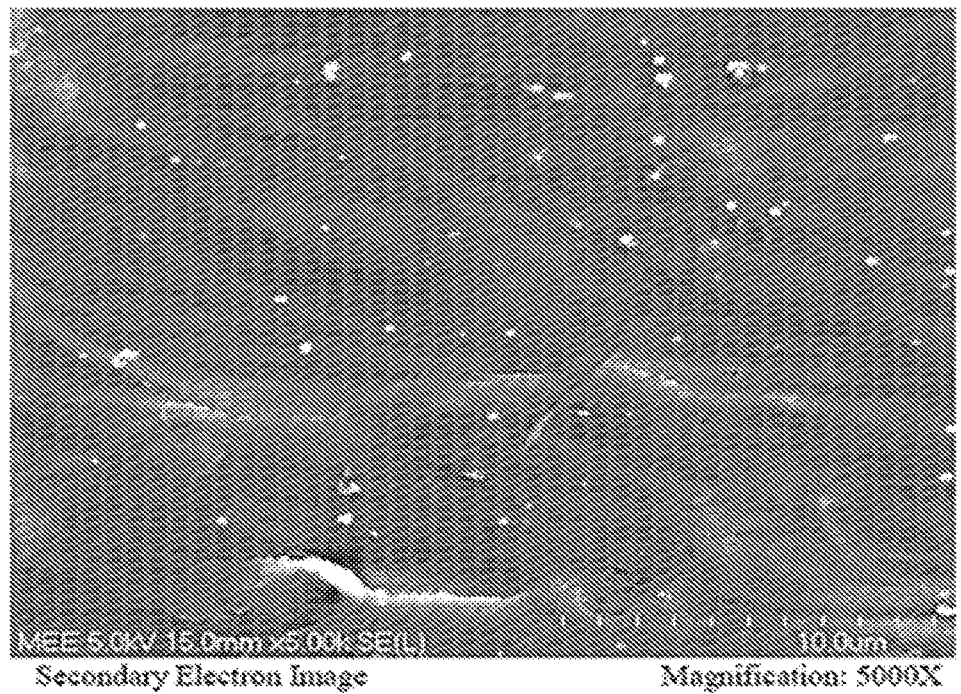
FIGS. 1A and 1B are SEM images comparing the structural physiology of a high-density polyethylene (HDPE)
Figure 1B:
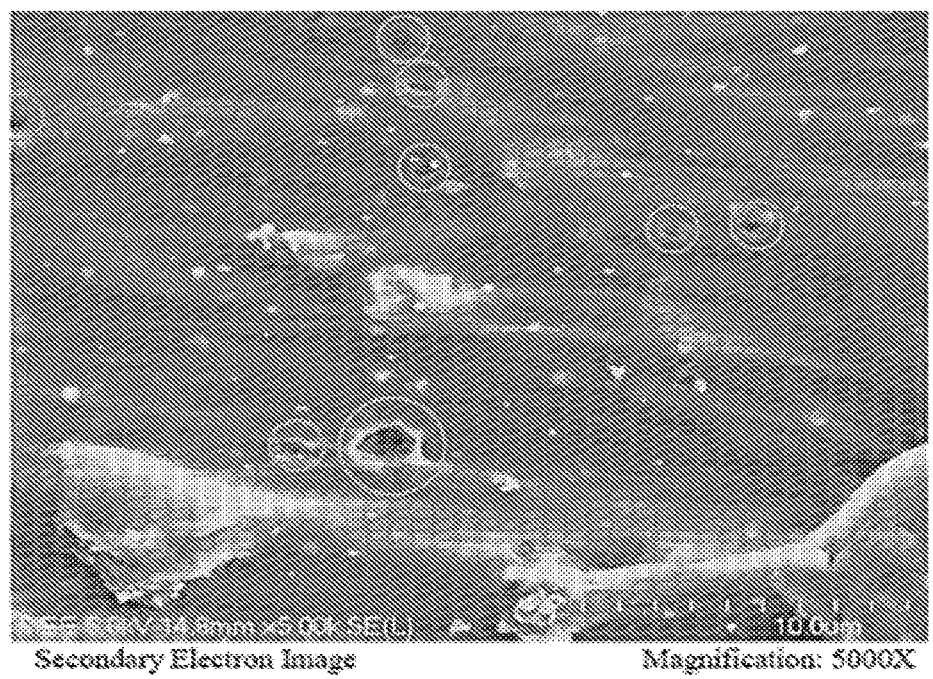

Scanning Electron Microscopy images were taken of an un-treated HDPE reference sample (FIG. 1A) and test sample (FIG. 1B). The test sample was incubated for two-months in minimal media (pH=7.0 at 30° C.) with weekly inoculation and media replacement identical to the Treatment-2 preparation. SEM imaging showed both reference and test samples as having similarly rough surfaces with many small bright particles and a somewhat fibrous morphology. SEM images of the reference sample showed no visible pocketing or cavitation. SEM images of the test sample showed visible changes to the surface morphology of the HDPE material (when compared to the reference sample) with increased cavitation, potentially due to microbes consuming or burrowing into the HDPE film.

Results from combined initial and duplicate experiments (n=8) including outliers were assessed using one-way analysis of variance (ANOVA) to determine the statistical significance of treatment on the difference between initial and final HDPE weight in milligrams. FIG. 6A shows the differences between initial and final HDPE weight show degradation at 0.21 mg±0.11, 0.60 mg±0.43 and 0.56 mg±0.35 for control, treatment-1, and treatment-2 respectively (p=0.047). The p-value was stronger when using ANOVA fit to a general linear model to compare final weight to sample treatment with initial weight as a covariate. FIG. 6B shows degradation at 0.19%±0.09, 0.41%±0.17 and 0.41%±0.15 for control, treatment-1, and treatment-2 respectively (p=0.014; control vs. treatment-1 p=0.016; control vs. treatment-2 p=0.008).

Example 3

HDPE Decay in Landfill Simulator Model Preparation

A pilot-scale landfill simulator was constructed to study degradative effect of microbial and nutritional amendments on HDPE. The simulator was constructed using six cylinders loaded with a sandy brown loam soil and a granular layer separated by landscaping fabric (FIG. 3). Evolved leachate was collected in reservoirs and analyzed weekly using Hach TNT plus chemistries for changes in chemical oxygen demand (COD) and sulfate. Following chemical analysis, leachate was amended and recirculated for all samples.

Three preparations were made in duplicate—a Control containing only the minimal media, micronutrients and HDPE; Treatment-1 including the minimal media, MDG-8992, MDG-2112, micronutrients and HDPE; and Treatment-2 including the minimal media, MDG-4954, MDG-2310, micronutrients and HDPE. Pre-weighed HDPE film samples were surrounded by a proprietary blend of municipal solid waste, which was then suspended and compressed in the lower third of the soil-filled cylinders. Moisture levels were adjusted to field capacity and a proprietary blend of synthetic leachate was added to initial moisture amendments. Cylinders were incubated for two months at room temperature between 18 and 34° C. (pH=7.35±0.3). Evolved leachate (200 mL) was recirculated daily and amended weekly. Temperature and pH were recorded prior to and following leachate amendments. Amendments included water (adjusted to 200 mL), a pH buffer, a proprietary blend of micronutrients and the inoculation of treated preparations.

To remove biofilm and clean, HDPE film samples were soaked in a 2% sodium dodecyl sulfate (SDS) solution, washed with tap water, and rinsed with both 70% ethanol and deionized water. The film was dried at 55° C. for 72 hours and weighed on an analytical balance. The microbial degradation of HDPE was analyzed by measuring the dry-weight reduction of HDPE film, imaging with a scanning electron microscopy (SEM) and surface profile characterization using scanning white light interference microscopy (SWLIM).

Example 4

Results and Analysis From Landfill Simulator Model Preparation

The following calculation was used to calculate the dry-weight reduction of HDPE samples: % mass loss=[(initial weight minus final weight)/initial weight]×100. FIG. 7A shows the average differences between initial and final weight (mg) from samples incubated in the landfill simulator (n=2) show a decrease in weight at 1.5 mg, 2.15 mg and 1.70 mg. Percent degradation of HDPE film was 0.75%, 1.07% and 1.06% for control, treatment-1 and Treatment-2 respectively (FIG. 7B). The degradation rate in treated samples increased 30%.

Scanning Electron Microscopy images of HDPE film from the landfill simulator experiment were taken of Control and Treatment-2 samples (one replicate of the two) following incubation in the landfill simulator. Control sample (FIG. 2A) showed decreased cavitation when compared to the test sample (FIG. 2B), potentially due to microbes consuming or burrowing into the HDPE film. HDPE in the Control showed some visible pocketing and cavitation due to the non-sterile environment. Results from the surface profile characterization using SWLIM showed increased roughness, higher peaks and lower average valley depth in the test sample when compared to the control (Table 2).

TABLE 2

Results from surface profile characterization using scanning white light interference microscopy (SWLIM) show increased roughness, higher peaks and lower average valley depth in the test sample when compared to the control.
MVA12005
*Rku, Rsk: no units
All other measurements: nm

| Sample | Ra | Rku | Rp | Rpm | Rq | *Rsk | Rt | Rv | Rvm | Rz |
|---|---|---|---|---|---|---|---|---|---|---|
| Test Sample | | | | | | | | | | |
| 12005ac0439_1 | 330.8 | 3.1 | 1844.8 | 1654.5 | 416.4 | 0.2 | 4673.5 | −2828.6 | −2069.0 | 3723.5 |
| 12005ac0439_2 | 317.6 | 3.7 | 2072.5 | 1891.4 | 407.2 | 0.3 | 4792.0 | −2719.5 | −2051.3 | 3942.7 |
| 12005ac0439_3 | 328.2 | 3.1 | 1621.9 | 1515.8 | 412.3 | 0.2 | 4204.9 | −2583.0 | −2020.1 | 3535.7 |
| 12005ac0439_4 | 357.6 | 3.3 | 2102.6 | 1878.5 | 453.5 | 0.2 | 5161.2 | −3058.6 | −2356.2 | 4234.7 |
| 12005ac0439_5 | 330.1 | 3.3 | 2080.5 | 1881.6 | 416.2 | 0.3 | 5271.6 | −3191.1 | −1899.0 | 3780.6 |
| 12005ac0439_6 | 419.2 | 4.6 | 3812.8 | 3095.9 | 542.1 | 0.4 | 8137.9 | −4325.1 | −2735.2 | 5831.1 |
| 12005ac0439_7 | 650.3 | 2.9 | 2888.3 | 2676.7 | 810.8 | 0.0 | 6448.4 | −3560.1 | −2644.4 | 5321.1 |
| 12005ac0439_8 | 335.8 | 8.8 | 3610.8 | 3256.8 | 455.4 | 1.2 | 5756.9 | −2146.1 | −1749.3 | 5006.1 |
| 12005ac0439_9 | 367.1 | 4.2 | 2916.5 | 2395.5 | 472.4 | 0.6 | 5549.5 | −2632.9 | −2048.0 | 4443.5 |
| 12005ac0439_10 | 549.6 | 4.0 | 3865.9 | 3453.3 | 706.1 | 0.7 | 7884.9 | −4018.9 | −2430.9 | 5884.2 |
| Average | 398.6 | 4.1 | 2681.7 | 2370.0 | 509.2 | 0.4 | 5788.1 | −3106.4 | −2200.3 | 4570.3 |
| Std. Dev. | 112.5 | 1.7 | 852.1 | 709.7 | 139.5 | 0.4 | 1325.5 | 681.5 | 324.9 | 882.1 |
| Control Sample | | | | | | | | | | |
| 12005ac0440_1 | 331.3 | 3.1 | 1843.5 | 1644.0 | 416.2 | 0.1 | 4966.7 | −3123.2 | −2164.1 | 3809.1 |
| 12005ac0440_2 | 315.0 | 3.9 | 2172.6 | 2047.9 | 400.4 | 0.3 | 6247.8 | −4075.2 | −2746.8 | 4794.7 |
| 12005ac0440_3 | 375.3 | 3.1 | 2255.3 | 1969.0 | 472.2 | 0.1 | 5091.0 | −2835.7 | −2206.0 | 4174.9 |
| 12005ac0440_4 | 442.6 | 2.8 | 2306.2 | 2072.1 | 550.1 | 0.5 | 5063.2 | −2757.0 | −2169.7 | 4261.9 |
| 12005ac0440_5 | 310.1 | 3.0 | 1766.1 | 1520.0 | 389.5 | 0.2 | 3801.3 | −2035.2 | −1636.6 | 3156.5 |
| 12005ac0440_6 | 368.1 | 6.1 | 3421.0 | 3138.7 | 482.7 | 0.7 | 5859.5 | −2438.5 | −1841.0 | 4979.7 |
| 12005ac0440_7 | 340.5 | 3.2 | 1744.6 | 1672.8 | 428.4 | 0.2 | 5425.5 | −3680.9 | −2506.8 | 4179.6 |
| 12005ac0440_8 | 393.6 | 3.3 | 2741.0 | 2285.0 | 495.6 | 0.2 | 4877.4 | −2136.5 | −1897.0 | 4182.0 |
| 12005ac0440_9 | 311.2 | 3.1 | 1965.5 | 1702.5 | 389.5 | 0.2 | 4651.1 | −2685.6 | −2083.1 | 3785.6 |
| 12005ac0440_10 | 338.5 | 3.4 | 2055.8 | 1876.2 | 430.5 | 0.2 | 4409.6 | −2353.7 | −1867.0 | 3743.1 |
| Average | 352.6 | 3.5 | 2227.2 | 1992.8 | 445.5 | 0.2 | 5039.3 | −2812.1 | −2113.8 | 4106.6 |
| Std. Dev. | 42.5 | 0.9 | 515.3 | 465.9 | 52.9 | 0.2 | 699.0 | 656.3 | 330.5 | 527.3 |

Ra-roughness average
Rku-keotosis
Rp-maximum profile peak height
Rpm-average maximum profile peak height
Rq-root mean square roughness (ms)
Rsk-skewness
Rt-maximum height of the profile
Rv-maximum profile valley depth
Rvm-average maximum profile valley depth
Rz-average maximum height of the profile Table 3 includes the projected time to complete degradation assuming a simple linear rate in a simulated landfill environment for each of the sample preparations. The data showed that in a simulated landfill environment, complete degradation of HDPE would take 21 years, 14 years, and 15 years for the Control, Treatment-1 and Treatment-2, respectively. When comparing the averaged treated results to the control for landfill simulator, there is a six-year difference degradation rates for treated samples. If pilot testing results could be scaled to field testing, the bioaugmentation of incoming waste could reduce plastic by 30%.

TABLE 3

Projected Time to Complete Degradation Given Constant Rate.

| Sample | % Average | Years to Degrade |
|---|---|---|
| Control | 0.75 | 21 |
| Treatment-1 | 1.07 | 14 |
| Treatment-2 | 1.06 | 15 |

Table 4 presents a comparison for the average HDPE degradation in years if a simple linear rate of degradation is assumed for samples incubated in minimal media (including the initial experiment excluding outliers and combined experiments including outliers) and a simulated landfill environment for all sample preparations (Control, Treatment-1 and Treatment-2). Results from incubation in the landfill simulator show a higher rate of degradation when compared to incubation in minimal media despite decreased moisture content (approximately 12% at field capacity), oxygen, dosage, nutrients and temperature, which could be attributed to the native microbial communities and extra nutrients from municipal solid waste in the simulator.

TABLE 4

Results comparing years to degrade assuming a simple linear rate for the initial experiment in minimal media excluding outliers, combined duplicate experiments in minimal media including outliers, and results from incubation in a simulated landfill environment.

| | Initial minimal media Experiment (n = 4) | | Combined minimal media experiments (n = 8) | | Landfill simulator (n = 2) | |
|---|---|---|---|---|---|---|
| Sample | % Average | Years | % Average | Years | % Average | Years |
| Control | 0.09 ± 0.05 | 171 | 0.19 ± 0.09 | 81 | 0.75 | 21 |
| Treatment-1 | 0.52 ± 0.19 | 30 | 0.41 ± 0.17 | 38 | 1.07 | 14 |
| Treatment-2 | 0.43 ± 0.04 | 36 | 0.41 ± 0.15 | 38 | 1.06 | 15 |

Biological and nutritional leachate amendments lowered the COD for all samples with increased reduction in treated preparations compared to the control (n=2). COD was reduced by 27%, 38% and 41% for control, treatment-1, and treatment-2 respectively (reduction from weeks 2-8 in FIG. 8). Sulfate was reduced below detectable levels for all samples at a minimum of 83%, 77%, and 81% for control, treatment-1, and treatment-2 respectively (reduction from weeks 3-8 in FIG. 9).

In addition to the reduction of plastics, the biological treatment of leachate, nutrient amendments and recirculation have potential improve leachate quality. When COD and leachate toxicity is decreased, there is an increase in the availability of nutrients to native microbial consortia which promotes the uptake and metabolization of potentially harmful chemicals, thus deterring surface and groundwater contamination. In addition, the recirculation of treated leachate (common in bioreactor landfills) could act as a multiplier in dosage rates. With enhanced waste stabilization and improved leachate quality, it is possible for the thirty years of post-closure care costs to be reduced and the land promptly reclaimed.

Microbial inoculants and nutrients could be applied using a sprayer truck to either the daily fill cover or directly to incoming waste. Alternate applications include the dosing of leachate ponds and lift stations to improve leachate quality. Continued research on bioaugmentation is warranted to optimize application rate and further understand the endproducts of degradation.

Example 5

Biofilm Formation on HDPE Surface HDPE in Minimal Media Preparation

Minimal media containing high-density polyethylene (HDPE) as a sole carbon source was augmented with isolated strains of *Bacillus subtilis* and *Bacillus amyloliquefaciens* and micronutrients. One preparation was made with Treatment-2 including the minimal media, MDG-4954, MDG-2310, micronutrients and HDPE. Inoculation and media replacement occurred weekly over two months (pH=7.0 at 30° C.). Post incubation, an unwashed HDPE sample was sent for SEM imaging to examine the HDPE film surface for the presence of *Bacillus* sp. The HDPE film was removed from the solution and a few small pieces were cut from the film. The pieces were allowed to dry and were sputter coated with a thin film of gold-palladium to facilitate high-resolution SEM. Four separate areas were examined and micrographs acquired. SEM images of un-washed HDPE film show surface cleavage and colonization with rod-shaped particles about 1 to 2 μm long consistent with the morphology of *Bacillus* microbes. This implies the initiation of degradation via microbial biofilm formation (FIGS. 4A, FIG. 4B and FIG. 4C).

Example 6

Strain Identification and Uniqueness

The Randomly Amplified Polymorphic DNA PCR method (hereafter referred to as RAPD-PCR) was used to identify genetic variability of each strain. Preparation of the DNA to be used in the RAPD-PCR reaction was done by using the QIAGEN® Tissue and Blood single column kit (QIAGEN®, Venlo, The Netherlands). FIG. 10 illustrates RAPD-PCR results for strains 2112, 8992, 4954, and 2310, with the first and last lanes being a molecular weight ladder. The results show that all four strains are unique from each other.

What is claimed is:

1. A commercial package comprising an isolated *Bacillus* strain selected from the group consisting of *Bacillus* strain 8992 (NRRL No. B-67472), *Bacillus* strain 2112 (NRRL No. B-67473), *Bacillus* strain 4954 (NRRL No. B-67474), *Bacillus* strain 2310 (NRRL No. B-67471), and combinations thereof.

2. The commercial package of claim 1 wherein the *Bacillus* strain is in the form of a powder, a freeze-dried composition, a pellet or a gel.

3. The commercial package of claim 1 further comprising a carrier for the *Bacillus* strain.

4. The commercial package of claim 3 wherein the carrier is selected from the group consisting of a salt, mineral oil, a dextrin, whey, sugar, limestone, dried starch, sodium silico aluminate, and combinations thereof.

5. The commercial package of claim 4 wherein the *Bacillus* strain is in liquid form.

6. The commercial package of claim 1 further comprising a binder selected from the group consisting of clay, yeast cell wall components, aluminum silicate, glucan, and combinations thereof.

7. The commercial package of claim 1 comprising live *Bacillus* strain cells.

8. The commercial package of claim 1 comprising *Bacillus* strain spores.

9. The commercial package of claim 1 wherein said *Bacillus* strain is 8992 (NRRL No. B-67472).

10. The commercial package of claim 1 wherein said *Bacillus* strain is 2112 (NRRL No. B-67473).

11. The commercial package of claim 1 wherein said *Bacillus* strain is 4954 (NRRL No. B-67474).

12. The commercial package of claim 1 wherein said *Bacillus* strain is 2310 (NRRL No. B-67471).

13. A waste additive composition comprising an isolated *Bacillus* strain selected from the group consisting of *Bacillus* strain 8992 (NRRL No. B-67472), *Bacillus* strain 2112 (NRRL No. B-67473), *Bacillus* strain 4954 (NRRL No. B-67474), *Bacillus* strain 2310 (NRRL No. B-67471), and combinations thereof.

14. The waste additive composition of claim 13 wherein the *Bacillus* strain is lyophilized and is in the form of a powder, a freeze-dried composition, a gel or a pellet.

15. The waste additive composition of claim 13, wherein the *Bacillus* strain degrades a plastic.

16. The waste additive composition of claim 13, wherein the *Bacillus* strain produces an enzyme selected from the group consisting of an a hydrolase, an oxidoreductase, a galactosidase, an NSPase, a phytase, an arabinoxylanase, a cellulase, a hemicellulase, a protease, an amylase, a xylanase, an esterase, a lipase, and combinations thereof.

17. The waste additive composition of claim 13, further comprising an exogenously added micronutrient.

18. The waste additive composition of claim 17, wherein said micronutrient is selected from nitrogen, phosphorus and combinations thereof.

19. The waste additive composition of claim 13, further comprising a binder selected from the group consisting of clay, yeast cell wall components, aluminum silicate, glucan and combinations thereof.

20. The waste additive composition of claim 13, further comprising one or more purified enzymes added to said composition, wherein said enzymes are selected from the group consisting of a hydrolase, an oxioreductase, a galactosidase, an NSPase, a phytase, an arabinoxylanase, a cellulase, a hemicellulase, a protease, an amylase, a xylanase, an esterase, a lipase, and combinations thereof.

21. The waste additive composition of claim 13, wherein said composition comprises two or more *Bacillus* strains selected from the group consisting of *Bacillus* strain 8992 (NRRL No. B-67472), *Bacillus* strain 2112 (NRRL No. B-67473), *Bacillus* strain 4954 (NRRL No. B-67474), and *Bacillus* strain 2310 (NRRL No. B-67471).

* * * * *